US010739331B2

(12) United States Patent
MacMillan-Crow

(10) Patent No.: US 10,739,331 B2
(45) Date of Patent: Aug. 11, 2020

(54) OMA1 ACTIVITY ASSAY

(71) Applicant: BioVentures, LLC, Little Rock, AR (US)

(72) Inventor: Lee Ann MacMillan-Crow, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 0 days.

(21) Appl. No.: 16/101,134

(22) Filed: Aug. 10, 2018

(65) Prior Publication Data

US 2019/0049430 A1    Feb. 14, 2019

Related U.S. Application Data

(60) Provisional application No. 62/544,538, filed on Aug. 11, 2017.

(51) Int. Cl.
| | |
|---|---|
| *C07K 14/705* | (2006.01) |
| *G01N 33/50* | (2006.01) |
| *C12N 9/64* | (2006.01) |
| *G01N 33/94* | (2006.01) |
| *G01N 33/68* | (2006.01) |
| *G01N 33/58* | (2006.01) |

(52) U.S. Cl.
CPC ....... *G01N 33/5008* (2013.01); *C07K 14/705* (2013.01); *C12N 9/6416* (2013.01); *C12N 9/6489* (2013.01); *G01N 33/582* (2013.01); *G01N 33/6893* (2013.01); *G01N 33/94* (2013.01); *C07K 2319/02* (2013.01); *C07K 2319/03* (2013.01); *C07K 2319/07* (2013.01); *C07K 2319/33* (2013.01); *C07K 2319/50* (2013.01); *C07K 2319/60* (2013.01); *C07K 2319/70* (2013.01); *G01N 2333/705* (2013.01); *G01N 2333/96419* (2013.01); *G01N 2800/7066* (2013.01)

(58) Field of Classification Search
None
See application file for complete search history.

(56) References Cited

U.S. PATENT DOCUMENTS

| | | | | |
|---|---|---|---|---|
| 7,157,575 B2 * | 1/2007 | Tsien | ............... | C07D 501/00 540/205 |
| 7,160,996 B1 * | 1/2007 | Cook | ............... | C07H 21/04 536/24.3 |

OTHER PUBLICATIONS

McBride et al., Mitochondrial Function: OMA1 and OPA1, the Grandmasters of Mitochondrial Health, 2010, Current Biology vol. 20 No. 6, R274, 3 pages (Year: 2010).*
Tobacyk et al., The first direct activity assay for the mitochondrial protease OMA1, Mar. 26, 2019, Mitochondrion 46: 1-5 (Year: 2019).*
Acin-Perez, R. et al., "Ablation of the stress protease OMA1 protects against heart failure in mice," Sci. Transl. Med., Mar. 28, 2018, pp. 1-14, vol. 10, eaan4935.
Anand, R. et al., "Proteolytic control of mitochondrial function and morphogenesis," Biochim. Biophys. Acta., 2013, pp. 195-204, vol. 1833.
Anand, R. et al., "The i-AAA protease YME1L and OMA1 cleave OPA1 to balance mitochondrial fusion and fission," J. Cell Biol., 2014, pp. 919-929, vol. 204, No. 6, The Rockefeller University Press.
Baker, M. et al., "Stress-induced OMA1 activation and autocatalytic turnover regulate OPA1-dependent mitochondrial dynamics," EMBO J., 2014, pp. 578-593, vol. 33, No. 6.
Bohovych, I. et al., "Stress-triggered activation of the metalloprotease Oma1 involves its C-terminal region and is important for mitochondrial stress protection in yeast," J Biol Chem., May 2014, pp. 13259-13272, vol. 289, No. 19.
Chen, H. et al., "Mitochondrial dynamics—fusion, fission, movement, and mitophagy—in neurodegenerative diseases," Hum. Mol. Genet., 2009, pp. R169-R176, vol. 18, No. 2.
Colbere-Garapin, F. et al., "A New Dominant Hybrid Selective Marker for Higher Eukaryotic Cells," J. Mol. Biol., Jul. 25, 1981, pp. 1-14, vol. 150, No. 1.
Cone, R. et al., "High-efficiency gene transfer into mammalian cells: Generation of helper-free recombinant retrovirus with broad mammalian host range," PNAS, Oct. 1984, pp. 6349-6353, vol. 81.
Gribskov, M. et al., "Sigma factors from *E. coli, B. subtilis*, phage SP01, and phage T4 are homologous proteins," Nucl. Acids Res., 1986, pp. 6745-6763, vol. 14, No. 16, IRL Press Limited, Oxford, England.
Hartman, S. et al., "Two dominant-acting selectable markers for gene transfer studies in mammalian cells," PNAS, Nov. 1988, pp. 8047-8051, vol. 85.
Head, B. et al., "Inducible proteolytic inactivation of OPA1 mediated by the OMA1 protease in mammalian Cells," J. well Biol., 2009, pp. 959-966, vol. 187, No. 7, The Rockefeller University Press.
Ishihara, N. et al., "Regulation of mitochondrial morphology through proteolytic cleavage of OPA1," EMBO J., 2006, pp. 2966-2977, vol. 25, No. 13.

(Continued)

*Primary Examiner* — John D Ulm
(74) *Attorney, Agent, or Firm* — Polsinelli PC

(57) ABSTRACT

The present disclosure relates to methods and compositions for detecting mitochondrial dysfunction. In particular, the disclosure relates to reporter molecules that are cleavable by the zinc metalloprotease Metalloendopeptidase OMA1 (OMA1). In each embodiment, the reporter molecules of the invention are particularly useful for drug discovery and detection of diseases associated with mitochondrial dysfunction.

19 Claims, 6 Drawing Sheets
(3 of 6 Drawing Sheet(s) Filed in Color)
Specification includes a Sequence Listing.

(56) References Cited

OTHER PUBLICATIONS

Kaser, M. et al., "Oma1, a Novel Membrane-bound Metallopeptidase in Mitochondria with Activities Overlapping with the m-AAA Protease," J. Biol. Chem., Nov. 21, 2003, pp. 46414-46423, vol. 278, No. 47.
Khalimonchuk, O. et al., "Selective Oma1 Protease-mediated Proteolysis of Cox1 Subunit of Cytochrome Oxidase in Assembly Mutants," J. Biol. Chem., Mar. 2, 2012, pp. 7289-7300, vol. 287, No. 10.
Kong, B. et al., "p53 is Required for Cisplatin-induced Processing of the Mitochondrial Fusion Protein L-Opa1 That is Mediated by the Mitochondrial Metallopeptidase Oma1 in Gynecologic Cancers," J. Biol. Chem., Sep. 26, 2014, pp. 27134-27145, vol. 289, No. 39.
Korwitz, A. et al., "Loss of OMA1 delays neurodegeneration by preventing stress-induced OPA1 processing in mitochondria," J. Cell Biol., 2016, pp. 157-166, vol. 212, No. 2, The Rockefeller University Press.
Lee, S-J. et al., "Proliferin Secreted by Cultured Cells Binds to Mannose 6-Phosphate Receptors," J. Biol. Chem., Mar. 5, 1988, pp. 3521-3527, vol. 263, No. 7.
Leonard, A. et al., "Quantitative analysis of mitochondrial morphology and membrane potential in living cells using high-content imaging, machine learning, and morphological binning," Biochim. Biophys. Acta., 2015, pp. 348-360, vol. 1853, No. 2.
Logan, J. et al., "Adenovirus tripartite leader sequence enhances translation of mRNAs late after infection," PNAS, Jun. 1984, pp. 3655-3659, vol. 81.
Lowy, I. et al., "Isolation of Transforming DNA: Cloning the Hamster aprt Gene," Cell, 1980, pp. 817-823, vol. 22.
Mackett, et al., "Vaccinia virus: A selectable eukaryotic cloning and expression vector," PNAS, Dec. 1982, pp. 7415-7419, vol. 79.
Mackett, M. et al., "General Method for Production and Selection of Infectious Vaccinia Virus Recombinants Expressing Foreign Genes," J. Virol., Mar. 1984, pp. 857-864, vol. 49, No. 3.
Mishra, P. et al., "Proteolytic Cleavage of Opa1 Stimulates Mitochondrial Inner Membrane Fusion and Couples Fusion to Oxidative Phosphorylation," Cell Metab., Apr. 1, 2014, pp. 630-641, vol. 19.
Mishra, P. et al., "Mitochondrial Dynamics is a Distinguishing Feature of Skeletal Muscle Fiber Types and Regulates Organellar Compartmentalization." Cell Metab., Dec. 1, 2015, pp. 1033-1044, vol. 22, No. 6.
Mulligan, R. et al., "Selection for animal cells that express the *Escherichia coli* gene coding for xanthine-guanine phosphoribosyltransferase," PNAS, Apr. 1981, pp. 2072-2076, vol. 78, No. 4.
O'Hare, K. et al., "Transformation of mouse fibroblasts to methotrexate resistance by a recombinant plasmid expressing a prokaryotic dihydrofolate reductase," PNAS, Mar. 1981, pp. 1527-1531, vol. 78, No. 3.
Olichon, A. et al., "Loss of OPA1 Perturbates the Mitochondrial Inner Membrane Structure and Integrity, Leading to Cytochrome c Release and Apoptosis," J. Biol. Chem., Mar. 7, 2003, pp. 7743-7746, vol. 278, No. 10.
Olichon, A. et al., "Mitochondrial dynamics and disease, OPA1," Biochim. Biophys. Acta., 2006, pp. 500-509, vol. 1763, Nos. 5-6.
Ong, S-B. et al., "Mitochondrial Dynamics in Cardiovascular Health and Disease," Antioxid. Redox Signal., 2013, pp. 400-414, vol. 19, No. 4, Mary Ann Liebert, Inc.
Panicali, D. et al., "Construction of poxvirus as cloning vectors: Insertion of the thymidine kinase gene from herpes simplex virus into the DNA of infectious vaccinia virus," PNAS, Aug. 1982, pp. 4927-4931, vol. 79.
Parajuli, N. et al., "Renal cold storage followed by transplantation impairs expression of key mitochondrial fission and fusion proteins," PLoS One, Oct. 4, 2017, pp. 1-15, vol. 12, No. 10, e0185542.
Quiros, P. et al., "Loss of mitochondrial protease OMA1 alters processing of the GTPase OPA1 and causes obesity and defective thermogenesis in mice," EMBO J., 2012, pp. 2117-2133, vol. 31, No. 9.
Rainbolt, T. et al., "YME1L degradation reduces mitochondrial proteolytic capacity during oxidative stress," EMBO Rep., 2015, pp. 97-106, vol. 16, No. 1.
Rainbolt, T. et al., "Reciprocal Degradation of YME1L and OMA1 Adapts Mitochondrial Proteolytic Activity during Stress," Cell Rep., Mar. 8, 2016, pp. pp. 2041-2049, vol. 14, No. 9.
Ruan, Y. et al., "Loss of Yme1L perturbates mitochondrial dynamics," Cell Death Dis., 2013, pp. 1-12, vol. 4, No. e896, Macmillan Publishers Limited.
Sarver, N. et al., "Bovine Papilloma Virus Deoxyribonucleic Acid: a Novel Eucaryotic Cloning Vector," Mol. Cell. Biol., Jun. 1981, pp. 486-496, vol. 1, No. 6.
Smith, T. et al., "Comparison of Biosequences," Adv. Applied Math., 1981, pp. 482-489, vol. 2, Academic Press, inc.
Szybalska, E. et al., "Genetics of Human Cell Lines, IV. DNA-Mediated Heritable Transformation of a Biochemical Trait," PNAS, 1962, pp. 2026-2034, vol. 48.
UniProtKB Accession 096E52, "OMA1 zinc metallopeptidase," Aug. 12, 2018; 8 pgs.
Vasquez-Trincado, C. et al., "Mitochondrial dynamics, mitophagy and cardiovascular disease," J. Physiol., 2016, pp. 509-525, vol. 594, No. 3.
Wai, T. et al., "Imbalanced OPA1 processing and mitochondrial fragmentation cause heart failure in mice," Sci., Dec. 4, 2015, pp. 1221, aad0116-1 to aad0116-11, vol. 350, No. 6265.
Wai, T. et al., "Mitochondrial Dynamics and Metabolic Regulation," Trends Endocrinol. Metab., Feb. 2016, pp. 105-117, vol. 27, No. 2.
Wigler, M. et al., Transfer of Purified Herpes Virus Thymidine Kinase Gene to Cultured Mouse Cells, Cell, May 1977, pp. 223-232, vol. 11.
Wigler, M. et al., "Transformation of mammalian cells with an amplifiable dominant-acting gene," PNAS, Jun. 1980, pp. 3567-3570, vol. 77, No. 6.
Xiao, X. et al., "OMA1 mediates OPA1 proteolysis and mitochondrial fragmentation in experimental models of schemic kidney injury," Am. J. Physiol. Renal Physiol., Mar. 26, 2014, pp. F1318-F1326, vol. 306, No. 11.
Zhang, K. et al., "Membrane depolarization activates the mitochondrial protease OMA1 by stimulating self-cleavage," EMBO Rep., 2014, pp. 576-585, vol. 15, No. 5.

* cited by examiner

OMA1 ACTIVITY ASSAY

CROSS REFERENCE TO RELATED APPLICATIONS

This application claims the benefit of U.S. Provisional Application No. 62/544,538, filed Aug. 11, 2017, the disclosure of which is hereby incorporated by reference in its entirety.

GOVERNMENTAL RIGHTS

This invention was made with government support under Grant No. GM106419 awarded by the National Institutes of Health. The government has certain rights in the invention.

FIELD OF THE TECHNOLOGY

The present disclosure relates generally to methods and compositions for detecting mitochondrial dysfunction. In particular, the disclosure relates to reporter molecules that are cleavable by the zinc metalloprotease Metalloendopeptidase OMA1 (OMA1). In each embodiment, the reporter molecules of the invention are particularly useful for drug discovery and detection of diseases associated with mitochondrial dysfunction.

BACKGROUND

Mitochondria are dynamic organelles of eukaryotic cells which fulfill numerous essential functions, including, ATP-generation, calcium signaling, phospholipid metabolism and apoptosis. A fundamental pathway utilized by cells to ensure mitochondria meet cellular demands is to govern the delicate balance between fusion and fission in the mitochondrial network. Mitochondrial dynamics are tightly regulated processes that occur in response to the cell environment or cellular differentiation. A disturbance of these dynamics, often observed under stress or pathologic conditions, causes mitochondrial fragmentation which can ultimately lead to cell death. Current methods for detecting mitochondrial dysfunction rely on the use of assays such as PCR and specific mutation analysis. Assaying disturbances in the dynamic regulation of the mitochondrial network is difficult requiring specialized cellular imaging techniques, which generally can be time-consuming and costly.

OMA1 is an important regulator of mitochondrial dynamics involved with normal quality control of the mitochondrial network. OMA1 expression is induced with stress to mitochondria and increased OMA1 activity promotes mitochondrial fragmentation. Current methods for assaying OMA1 activity utilize an indirect method through western blotting by determining the proteolytic processing status of the inner mitochondrial membrane-localized protein, dynamin-related GTPase optic atrophy type 1 (OPA1). However, OPA1 can be processed by multiple proteases, complicating the analysis of OMA1 activity.

Thus, there is a need for a technology which allows for the detection of OMA1 activity in a sensitive, direct and efficient manner. Additionally, there is a need for high throughput screening methods useful for drug discovery and detection of diseases associated with mitochondrial dysfunction.

SUMMARY

Among the various aspects of the present disclosure is the provision of an isolated reporter molecule, wherein the reporter molecule comprises at least one protease cleavage site recognized by OMA1, at least one detection domain capable of emitting a signal and at least one repressor domain linked to the reporter molecule which represses the signal of the detection domain. In various aspects the detection domain emits a signal upon cleavage of the reporter molecule at the OMA1 cleavage site. The reporter molecule may include additional features which, for example, increase the cell-penetrating ability or which targets the reporter molecule to a distinct sub-cellular compartment or organelle, for example, mitochondria.

In an aspect the disclosure provides a method of identifying mitochondrial dysfunction. The method includes providing to a biological sample a reporter molecule comprising a detection domain capable of emitting a signal linked to a linker domain comprising an OMA1 cleavage site and a repressor domain operably linked to the linker domain which represses the signal of the detection domain, and wherein cleavage of the linker domain at the OMA1 cleavage site increases the signal of the detection domain. The method includes measuring the signal of the detection domain, wherein an increase in the signal of the detection domain indicates mitochondrial dysfunction when compared to a biological sample without mitochondrial dysfunction.

In another aspect the disclosure provides a method of identifying compounds useful for treating mitochondrial dysfunction. The method includes providing to a biological sample a test compound and a reporter molecule, the reporter molecule comprising; a detection molecule capable of emitting a signal linked to a linker domain comprising an OMA1 cleavage site, a repressor molecule that represses the signal of said detection domain, wherein the repressor molecule is operably linked to the linker domain, and wherein cleavage of said linker domain at said protease cleavage site increases the signal of said detection domain. The method includes contacting said biological sample with said test compound under conditions sufficient for said components to interact; and measuring the activity of said reporter, wherein reduced signal of the reporter indicates an ability of the compound to treat mitochondrial dysfunction by reducing OMA1 protease activity relative to an untreated control.

In another aspect the disclosure provides a method of identifying compounds useful in modulating the activity of OMA1. The method includes providing to a biological sample a test compound and a reporter molecule, the reporter molecule comprising; a detection molecule capable of emitting a signal linked to a linker domain comprising an OMA1 cleavage site, a repressor molecule that represses the signal of said detection domain, wherein the repressor molecule is operably linked to the linker domain, and wherein cleavage of said linker domain at said protease cleavage site increases the signal of said detection domain. The method includes contacting said biological sample with said test compound under conditions sufficient for said components to interact; and measuring the activity of said reporter. In some embodiments, if the signal of the detection domain is reduced relative to an untreated control indicates the compound is useful for reducing OMA1 protease activity. In some embodiments, if the signal of the detection domain is increased relative to an untreated control indicates the compound is useful for activating OMA1 protease activity.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE FIGURES

The application file contains at least one drawing executed in color. Copies of this patent application publication with color drawing(s) will be provided by the Office upon request and payment of the necessary fee.

FIG. 1A shows current methods utilizing western blotting for OPA1 as a means for detecting mitochondria dysfunction. FIG. 1B shows the basis of the OMA1 activity assay using FRET technology. Fluorescence emission at 405 nm is increased when OMA1 recognizes and cleaves the OPA1 peptide presumably between the arginine and alanine residues. MCA (7-Methoxycoumarin-4-ylacetyl) serves as the fluorophore and DNP (2,4-Dinitrophenyl) the quencher. (SEQ ID NO:1)

FIG. 2A shows a dose response of OPA1 FRET substrate concentrations (1, 5, 10, 15, 20 and 30 μM) on the rate of the reaction was used to determine the Km and Vmax values. Michalis-Menten kinetics of the average slope (FLS/min) for each substrate concentration resulted in values of Km=7.1 uM and Vmax=34.6. FIG. 2B shows a time course of OMA1 activity assay using untreated NRK cells with 5 μM of OPA1 FRET substrate resulted in a linear increase in fluorescence (FLS) over 30 min. Data is expressed as mean±SEM; n=3.

FIG. 3A shows protein lysates (5 μg) from NRK cells treated with OMA1 siRNA (50 nM; 24 h; 37° C.) have reduced OMA1 activity, *p=0.015. FIG. 3B shows protein lysates from NRK cells treated with YME1L siRNA (50 nM; 24 h; 37° C.) have an increase in OMA1 activity, *p=0.003. Insets show a representative image of OMA1 and YME1L knockdown using Western blots. Slopes (0-30 min) were converted to percent change from control/scramble rate (FLS/min) values. Data is expressed as mean±SEM; n=3-4.

FIG. 6A shows the scheme of mitochondrial targeted FRET-peptide. SS sequence containing D-Arginine (D-Arg), dimethyl tyrosine (Dmt), ornithine (Orn), tryptophan (Trp) followed by the specific peptide sequence within OPA1 that OMA1 cleaves, flanked by the fluorophore, MCA (7-Methoxycoumarin-4-ylacetyl), and quencher, DNP (2,4-Dinitrophenyl). FIG. 6B shows OMA1 activity in live-cells. (SEQ ID NO:1)

DETAILED DESCRIPTION

Figure 1A:
FIG. 1A and FIG. 1B illustrate methods of measuring OMA1 activity.

Provided herein are reporter molecules, which comprise a detection domain, a linker domain comprising an OMA1 cleavage site and a repressor domain that represses the signal of said detection domain. Also provided are methods of using the reporter molecules to detect mitochondrial dysfunction or identify compounds which are beneficial in the treatment of disease associated with mitochondrial dysfunction.

Various aspects of the invention are described in further detail in the following sections.

I. Reporter Molecules

One aspect of the present disclosure provides reporter molecules comprising a detection domain capable of emitting a signal. The reporter molecules also comprise a linker domain comprising an OMA1 cleavage site such that upon cleavage of the linker domain by OMA1, the signal of the detection domain is increased. The reporter molecules also comprise a repressor domain, which is operably linked to the linker domain such that when the linker domain is intact, the repressor domain represses the activity of the detection domain. Provided herein are isolated reporter molecules, isolated nucleic acids encoding the reporter molecules, and cells comprising nucleic acids encoding the reporter molecules.

A "reporter" molecule of the invention is any molecule in which a signal from the detection domain may be assayed in a sample. The sample may be a biological sample or an in vitro sample. In a non-limiting example, the assay may be a physical detection such as spectrophotometric detection of the reporter. As used herein, a "detection domain" is any type of label which, when attached to a reporter molecule renders the reporter molecule detectable. In general, a detection domain may include luminescent molecules, chemiluminescent molecules, fluorochromes, fluorophores, fluorescent quenching agents, colored molecules, radioisotopes, radionuclides, cintillants, massive labels such as a metal atom (for detection via mass changes), biotin, avidin, streptavidin, protein A, protein G, antibodies or fragments thereof, Grb2, polyhistidine, Ni2+, Flag tags, myc tags, heavy metals, enzymes, alkaline phosphatase, peroxidase, luciferase, electron donors/acceptors, acridinium esters, and colorimetric substrates. Many assays and detection schemes are well known to one of skill in the art for various reporter molecules and can be utilized with the subject invention.

In one aspect, the reporter molecule comprises a detection domain wherein the detection domain is a fluorescent molecule. Non-limiting examples of such a fluorescent molecule include 2-Aminobenzoyl (Abz), N-Methyl-antraniloyl (N-Me-ABZ), 5-(Dimethylamino)naphthalene-1-sulfonyl (Dansyl), 5-[(2-Aminoethyl)amino]-naphthalene-1-sulfonic acid (EDANS), 7-Dimethylaminocoumarin-4-acetate (DMACA), 6-Amino-2,3-dihydro-1,3-dioxo-2-hydrazinocarbonylamino-1H-benz[d,e]isoquinoline-5,8-disulfonic acid (Lucifer Yellow), Fluorescein isothiocyanate (FITC), (7-Methoxycoumarin-4-yl)acetyl (Mca), Tryptophan (Trp), and the like. In yet another non-limiting example, the fluorescent molecule is a fluorescent peptide such as a green fluorescent protein (GFP).

In yet another non-limiting example, the reporter molecule contains an epitope that can be bound by an antibody. A labeled form of the antibody or a secondary antibody that binds the antibody that in turn binds the reporter molecule can then be used to assay the presence of the antibody. One of skill in the art can readily determine a detection scheme useful for visualizing an immunological epitope with a specific antibody. In some embodiments, the repressor domain masks and prevents binding of the antibody to the detection domain when the linker domain is intact.

The reporter molecule comprises a linker domain to which the detection domain and repressor domain are attached. Cleavage of the linker domain results in the ability to detect the detection domain, for example by increasing the signal of the detection domain. A "linker domain" refers to a polypeptide containing a Metalloendopeptidase OMA1 cleavage site. Metalloendopeptidase OMA1, mitochondrial (also known as Metalloprotease-related protein 1 or Overlapping with the m-AAA protease 1 homolog) is an enzyme that in humans is encoded by the OMA1 gene. As a metalloprotease, this protein is a substantial component of the quality control system in the inner membrane of mitochondria. Being activated by enzyme Bax and Bak, mitochondrial protease OMA1 promotes cytochrome c release which subsequently induces apoptosis. The gene OMA1 encodes a metalloprotease, a founding member of a conserved family of membrane-embedded metallopeptidases in mitochondria. The human gene has 9 exons and locates at chromosome band 1p32.2-p32.1. The human protein metalloendopetidase OMA1, mitochondrial (UniProtKB accession Q96E52) is 60.1 kDa in size and composed of 524 amino acids with mitochondrial transition peptide (position 1-13).

As described above, the signal of the detection domain can be increased once it has lost its repressor domain through cleavage at the linker domain. It should be noted that the linker domain can be a synthetic polypeptide containing an OMA1 cleavage site. In another aspect, the linker domain maybe an integral part of, and therefore included in the detection domain or the repressor domain, so long as cleavage at the OMA1 cleavage site results in removal of the repressor from the reporter molecule and increases the signal of the detection domain.

A linker domain of the invention must be at least 3 amino acid residues. A linker domain of less than 3 amino acids will not work in a reporter molecule of the invention. In an embodiment, a linker domain may be 3 to 20 amino acid residues. In another embodiment, a linker domain may be 3 to 15 amino acid residues. In a specific embodiment, a linker domain comprises 3 to 10 amino acid residues. In another specific embodiment, a linker domain comprises 3 to 10 amino acid residues. In another specific embodiment, a linker domain comprises 3 to 9 amino acid residues. In another specific embodiment, a linker domain comprises 3 to 8 amino acid residues. In another specific embodiment, a linker domain comprises 3 to 7 amino acid residues. In another specific embodiment, a linker domain comprises 3 to 6 amino acid residues. In another specific embodiment, a linker domain comprises 3 to 5 amino acid residues. In another specific embodiment, a linker domain comprises 3 to 4 amino acid residues. In an exemplary embodiment, an amino acid residue linker comprises 8 residues. In a specific embodiment, an amino acid residue linker consists essentially of 3 to 20 residues. In another specific embodiment, an amino acid residue linker consists essentially of 3 or 10 residues. In an exemplary embodiment, an amino acid residue linker consists essentially of 8 residues.

In some embodiments, the linker domain comprises an 'RA motif'. The RA motif is a two amino acid motif consisting of an arginine residue followed by an alanine residue. In some embodiments, the 'RA' motif is the cleavage site recognized by OMA1. In some embodiments, the RA motif is flanked on one side or the other by the remaining linker domain amino acid residues. In some embodiments, the RA motif is flanked on both sides by the remaining linker domain amino acid residues.

In certain embodiments, a linker further comprises one or more spacers. Spacers are known in the art. Non-limiting examples of spacers include a lysine residue, poly-lysine residues, 2-aminoethoxy-2-ethoxy acetic acid (AEEA) linkers, AEEEA linkers, and AEA linkers. In a specific embodiment, a linker further comprises one or more 2-aminoethoxy-2-ethoxy acetic acid (AEEA) linkers.

In some embodiments, the linker domain comprises AFRATDHG (SEQ ID NO:1), GKTLLARAVAGEAD (SEQ ID NO:2), ALRATDHG (SEQ ID NO:3), DRWNEIRAQLLAQM (SEQ ID NO:4), LRESYERAKHILKT (SEQ ID NO:5), QHTIRAKQI (SEQ ID NO:6), WTTRAKERAFKQ (SEQ ID NO:7), GVVDRAQAG (SEQ ID NO:8), HTVRAKQI (SEQ ID NO:9), NSRRALL (SEQ ID NO:10), WTTRAKERAFKRQ (SEQ ID NO:11), EEIRAVGR (SEQ ID NO:12), SSTRRAYQQIL (SEQ ID NO:13), NKERAKREM (SEQ ID NO:14), GAGLRAAFG (SEQ ID NO:15), IYQRAFGG (SEQ ID NO:16), HRIRAKNT (SEQ ID NO:17), AMVTRAGLP (SEQ ID NO:18), VFGRACAL (SEQ ID NO:19), DLRRAKDI (SEQ ID NO:20), KTGRADIAN (SEQ ID NO:21), EQIRATIE (SEQ ID NO:22), GGRAIITK (SEQ ID NO:23), EWFRAGSA (SEQ ID NO:24), KGERADLI (SEQ ID NO:25), AARAAAAA (SEQ ID NO:26), or AFKATDHG (SEQ ID NO:27). In some embodiments, the linker domain is at least 60% homologous, at least 70% homologous, at least 71% homologous, at least 72% homologous, at least 73% homologous, at least 74% homologous, at least 75% homologous, at least 76% homologous, at least 77% homologous, at least 78% homologous, at least 79% homologous, at least 80% homologous, at least 80% homologous at least 81% homologous, at least 82% homologous, at least 83% homologous, at least 84% homologous, at least 85% homologous, at least 86% homologous, at least 87% homologous, at least 88% homologous, at least 89% homologous, at least 90% homologous, at least 91% homologous, at least 92% homologous, at least 93% homologous, at least 94% homologous, at least 95% homologous, at least 96% homologous, at least 97% homologous, at least 98% homologous, or at least 99% homologous to SEQ ID NOs: 1, 2, 3, 4, 5, 6, 7, 8, 9, 10, 11, 12, 13, 14, 15, 16, 17, 18, 19, 20, 21, 22, 23, 24, 25, 26 or 27.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website.

A "repressor" domain is a molecule capable of inhibiting or reducing the signal or activity or the ability to detect the detection domain. In some embodiments, the repressor acts interacts directly with the detection domain to repress its activity or function. In some embodiments, the repressor domain sterically blocks the detection domain thereby reducing the signal of the detection domain. In one aspect of the invention the repressor domain is a fluorescent quencher. As used herein a "quencher" is any molecule which decreases the fluorescence intensity of a given substance. In non-limiting examples, the repressor domain includes 2,4-Dinitrophenyl (Dnp), N-(2,4-Dinitrophenyl)ethylenediamine (EDDnp), 3-Nitro-tyrosine (3-Nitro-Tyr), 4-Nitrophenylalanine (4-Nitro-Phe), para-Nitroaniline (pNA), 4-(4-Dimethylaminophenylazo)benzoyl (DABCYL), 7-Nitrobenzo[2,1,3]oxadiazol-4-yl (NBD), 4-(4-Dimethylaminophenylazo)-benzenesulfonyl, 4-Nitro-benzyloxycarbonyl 4-Nitro-Z and the like. In another aspect, the detection domain and the repressor domain are fluorescent peptides, wherein a fluorescence energy transfer occurs between the two peptides. In one embodiment, the two peptides are linked by a linker domain comprising an OMA1 protease cleavage site, such that a different emission spectra is seen when the two fluorescent polypeptides are attached and when they are separated.

The reporter molecule of the invention may comprise further functional domains such that they increase the availability or targeting of the reporter molecule to a cell, cellular organelle or sub-cellular domain (e.g., cell-penetrating or translocation domains). In some embodiments, the fusion protein further comprises at least one additional domain. In one embodiment, the cell-penetrating domain can be a cell-penetrating peptide sequence derived from the HIV-1 TAT protein. As an example, the TAT cell-penetrating sequence can be GRKKRRQRRRPPQPKKKRKV (SEQ ID NO:28). In another embodiment, the cell-penetrating domain can be TLM (PLSSIFSRIGDPPKKKRKV; SEQ ID NO:29), a cell-penetrating peptide sequence derived from the human hepatitis B virus. In still another embodiment, the cell-penetrating domain can be MPG (GALFLGWLGAAGSTMGAPKKKRKV; SEQ ID NO:30 or GALFLGFLGAAGSTMGAWSQPKKKRKV; SEQ ID NO:31). In an additional embodiment, the cell-penetrating domain can be Pep-1 (KETWWETWWTEWSQPKKKRKV; SEQ ID NO:32), VP22, a cell penetrating peptide from Herpes simplex virus, or a polyarginine peptide sequence. The cell-penetrating domain can be located at the N-terminus, the C-terminus, or in an internal location of the protein. In another non-limiting example the additional domain may be a targeting domain which targets the reporter molecule to the mitochondria (e.g. mitochondrial targeting signal (MTS)). As an example the MTS can be amino terminal MLRTSSLFTRRVQPSLFRNILRLQST—(SEQ ID NO:33).

In some embodiments, the reporter molecule can be introduced into a biological sample, such as a cell, as an isolated protein. In some embodiments, the reporter molecule can further comprise at least one cell-penetrating domain, which facilitates cellular uptake of the protein. In addition, as a non-limiting example, upon uptake of the reporter molecule by the cell treatment with triphenylphosphonium-TPP can be used to direct the reporter molecule to the mitochondria of the cell.

II. Nucleic Acids Encoding Reporter Molecules

Another aspect of the present disclosure provides nucleic acids encoding any of the reporter molecules described above. The nucleic acid can be DNA or RNA. In one embodiment the DNA can be present in a vector. The nucleic acid sequences which encode the reporter molecule of the invention can be operatively linked to expression control sequences. "Operatively linked" refers to a juxtaposition wherein the components so described are in a relationship permitting them to function in their intended manner. An expression control sequence operatively linked to a coding sequence is achieved under conditions compatible with the expression control sequences. As used herein, the expression control sequences refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, and maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., Methods in Enzymology 153:516-544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the nucleic acid sequences encoding the fusion protein of the invention may be inserted into a recombinant expression vector. The term "recombinant expression vector" refers to a plasmid, virus or other vehicle known in the art that has been manipulated by insertion or incorporation of the nucleic acid sequences encoding the fusion peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 263:3521, 1988), baculovirus-derived vectors for expression in insect cells, cauliflower mosaic virus, CaMV; tobacco mosaic virus, TMV. The nucleic acid sequences encoding a fusion polypeptide of the invention can also include a localization sequence to direct the indicator to particular cellular sites by fusion to appropriate organellar targeting signals or localized host proteins. A polynucleotide encoding a localization sequence, or signal sequence, can be used as a repressor and thus can be ligated or fused at the 5' terminus of a polynucleotide encoding the reporter polypeptide such that the signal peptide is located at the amino terminal end of the resulting fusion polynucleotide/polypeptide. The construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989).

Depending on the vector utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516-544, 1987). These elements are well known to one of skill in the art.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., "Expression and Secretion Vectors for Yeast," in Methods in Enzymology, Eds. Wu & Grossman, 1987, Acad. Press, N.Y., Vol. 153, pp. 516-544, 1987; Glover, DNA Cloning, Vol. II, IRL Press, Wash., D.C., Ch. 3, 1986; and Bitter, "Heterologous Gene Expression in Yeast," Methods in Enzymology, Eds. Berger & Kimmel, Acad. Press, N.Y., Vol. 152, pp. 673-684, 1987; and The Molecular Biology of the Yeast *Saccharomyces*, Eds. Strathem et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: DNA Cloning Vol. 11, A Practical Approach, Ed. DM Glover, IRL Press, Wash., D.C., 1986). Alternatively, vectors may be used which promote integration of foreign DNA sequences into the yeast chromosome.

By "transformation" is meant a permanent genetic change induce in a cell following incorporation of new DNA (i.e., DNA exogenous to the cell). Where the cell is a mammalian cell, the permanent genetic change is generally achieved by introduction of the DNA into the genome of the cell.

By "transformed cell" is meant a cell into which (or into an ancestor of which has been introduced, by means of recombinant DNA techniques, a DNA molecule encoding a fusion protein consisting of an optical sensor operatively fused to a responsive polypeptide, or fragment thereof, which normally has two or more conformational shapes, and which undergoes a conformational change during a cell signaling event.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transfected with DNA sequences encoding the reporter molecules of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukarotic Viral Vectors, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*), or may be a mammalian cell. In one embodiment, the mammalian cell is a human cell.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to CHO, VERO, BHK, HeLa, COS, MDCK, Jurkat, HEK-293, and W138. In one embodiment, the eukaryotic cell is a human cell.

Mammalian cell systems which utilize recombinant viruses or viral elements to direct expression may be engineered. For example, when using adenovirus expression vectors, the nucleic acid sequences encoding a fusion protein of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fluorescent indicator in infected hosts (e.g., see Logan & Shenk, Proc. Natl. Acad. Sci. USA, 81:3655-3659, 1984). Alternatively, the vaccinia virus 7.5K promoter may be used. (e.g., see, Mackett, et al., Proc. Natl. Acad. Sci. USA, 79:7415-7419, 1982; Mackett, et al., J. Virol. 49:857-864, 1984; Panicali, et al., Proc. Natl. Acad. Sci. USA 79:4927-4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone & Mulligan, Proc. Natl. Acad. Sci. USA, 81:6349-6353, 1984). High level expression may also be achieved using inducible promoters, including, but not limited to, the metallothionine IIA promoter and heat shock promoters.

For long-term, high-yield production of recombinant proteins, stable expression may be preferred. Rather than using expression vectors which contain viral origins of replication, host cells can be transformed with the cDNA encoding a fusion protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk-, hgprt- or aprt-cells respectively. Also, antimetabolite resistance can be used as the basis of selection for dhfr, which confers resistance to methotrexate (Wigler, et al., Proc. Natl. Acad. Sci. USA, 77:3567, 1980; O'Hare, et al., Proc. Natl. Acad Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al, J. Mol. Biol 150:1, 1981); and hygro, which confers resistance to hygromycin (Santerre, et al., Gene 30: 147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

A reporter molecule of the invention can be produced by expression of nucleic acid encoding the protein in prokaryotes. These include but are not limited to microorganisms such as bacteria transformed with recombinant bacteriophage DNA, plasmid DNA or cosmid DNA expression vectors encoding a fusion protein of the invention. A primary advantage of the fusion proteins of the invention is that they are prepared by normal protein biosynthesis, thus completely avoiding organic synthesis and the requirement for customized unnatural amino acid analogs. The constructs can also be expressed in E. coli in large scale. Purification from bacteria is simplified when the sequences include tags for one-step purification by nickel-chelate chromatography. The construct can also contain a tag to simplify isolation of the fluorescent indicator. For example, a polyhistidine tag of, e.g., six histidine residues, can be incorporated at the amino terminal end of the fluorescent protein. The polyhistidine tag allows convenient isolation of the protein in a single step by nickel-chelate chromatography. The fusion proteins of the invention can also be engineered to contain a cleavage site to aid in protein recovery.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

III. Methods of Using Reporter Molecules

The invention also provides methods utilizing reporter molecules to detect mitochondrial dysfunction or identify compounds which are beneficial in the treatment of disease associated with mitochondrial dysfunction. In general, the method includes providing a biological sample a reporter molecule comprising a detection domain linked to a linker domain comprising an OMA1 cleavage site, and a repressor domain that represses the activity of said detection domain. The repressor domain is operably linked to the linker polypeptide, such that cleavage of said linker polypeptide at said OMA1 protease cleavage site increases the signal of said detection domain. The activity of reporter molecule is then measured over time and compared to the activity of a reporter molecule in a control sample. Suitable reporter molecules are those describe in Section I and II above.

In an aspect the disclosure provides a method of detecting mitochondrial dysfunction in a subject. The method includes obtaining a biological sample from the subject; providing to the biological sample a reporter molecule comprising a detection domain capable of emitting a signal linked to a linker domain comprising an OMA1 cleavage site and a repressor domain operably linked to the linker domain which represses the signal of the detection domain, wherein cleavage of said linker domain at said OMA1 cleavage site increases the signal of said detection domain, and measuring the signal of said detection domain. In some embodiments, the signal of the reporter molecule is compared to a reporter molecule in a control sample. In some embodiments the method further comprises classifying the subject as having an increased or decreased risk of mitochondrial dysfunction. In some embodiments, the subject is classified as having an increased risk of mitochondrial dysfunction if the signal of the reporter molecule is increased relative to a healthy control. In some embodiments, the subject is classified as having a decreased risk mitochondrial dysfunction if the signal of the reporter molecule is the same or decreased relative to a healthy control.

Additionally, a method for monitoring mitochondrial dysfunction in a subject may also be used to determine the response to treatment. As used herein, subjects who respond to treatment are said to have benefited from treatment. Responses to treatment are measured in clinical practice using tests well known in the art and are intended to refer to specific parameters measured during clinical trials and in clinical practice by a skilled artisan. For example, a method of detecting the reporter molecule may be performed on the biological sample of the subject prior to initiation of treatment. Then at a later time, a method of detecting the reporter molecule may be used to determine the response to treatment over time. For example, a method of detecting the reporter molecule may be performed on the biological sample of the same subject days, weeks, months or years following initiation of treatment. Accordingly, a method of detecting the reporter molecule may be used to follow a subject receiving treatment to determine if the subject is responding to treatment. If the signal of the reporter molecule is decreased relative to a sample prior to treatment, then the subject may be responding to treatment. If the signal of the reporter molecule increases or remains the same relative to a sample prior to treatment, then the subject may not be responding to treatment. These steps may be repeated to determine the response to therapy over time.

Any suitable control sample known in the art may be used. For example, a suitable control may be the signal of a reporter molecule in a biological sample obtained from a subject or group of subjects of the same species that has no detectable mitochondrial dysfunction. In another example, a suitable control may be the signal of the reporter molecule in a biological sample obtained from a subject or group of subjects of the same species that has detectable mitochondrial dysfunction as measured via standard methods. In another example, a suitable control may be a measurement of the reporter molecule in a reference sample obtained from the same subject. The reference sample comprises the same type of biological sample as the test sample, and may or may not be obtained from the subject when mitochondrial dysfunction was not suspected. A skilled artisan will appreciate that it is not always possible or desirable to obtain a reference sample from a subject when the subject is otherwise healthy. For example, in an acute setting, a reference sample may be the first sample obtained from the subject at presentation. In another example, when monitoring the effectiveness of a therapy, a reference sample may be a sample obtained from a subject before therapy began. In such an example, a subject may have suspected mitochondrial dysfunction but may not have other symptoms of mitochondrial dysfunction or the subject may have suspected mitochondrial dysfunction and one or more other symptom of mitochondrial dysfunction.

As used herein, the term "biological sample" may be, in non-limiting examples, a biological fluid, a tissue, a tissue homogenate, cells, a cellular lysate, a tissue or cell biopsy, skin cells, tumor or cancer cells, or any combination thereof. As used herein "cell" includes prokaryotic cells and eukaryotic cells. In one aspect, the cell is a yeast cell. In another aspect, the cell is a mammalian cell such as a human cell. In another aspect, the human cell is a kidney cell. In some embodiments, a biological sample refers to a sample obtained from a subject. Any biological sample containing OMA1 is suitable. Numerous types of biological samples are known in the art. In some embodiments, the biological sample is a tissue sample such as a tissue biopsy. In one aspect, the biopsied tissue may be processed into individual cells or an explant, or processed into a homogenate, a cell extract, a membranous fraction, or a ceramide extract. In other embodiments, the sample may be a bodily fluid. Non-limiting examples of suitable bodily fluids include blood, plasma, serum, urine, and saliva. In a specific embodiment, the biological sample is blood, plasma, or serum. In a specific embodiment, the biological sample is plasma. The fluid may be used "as is", the cellular components may be isolated from the fluid, or a fraction may be isolated from the fluid using standard techniques.

A method of the invention may be used to detect mitochondrial dysfunction in a subject that is a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc.

In another aspect the disclosure provides a method of identifying compounds useful for treating mitochondrial dysfunction. In another aspect the disclosure provides a method of identifying compounds useful in modulating the activity of OMA1. In general, the method includes providing to a biological sample a test compound and a reporter molecule comprising a detection molecule linked to a linker domain comprising an OMA1 cleavage site, and a repressor domain that represses the activity of said detection domain, wherein the repressor domain is operably linked to the linker and, and, wherein cleavage of said linker domain at said protease cleavage site increases the signal of said detection domain. The method includes contacting said biological sample with said test compound under conditions sufficient for said components to interact; and measuring the signal of said reporter molecule, wherein reduced signal of the reporter relative to the signal of a reporter molecule in a sample without the test compound indicates an ability of the compound to treat mitochondrial dysfunction by reducing OMA1 protease activity. If the signal of the reporter molecule is increased or remains the same relative to the signal of a reporter molecule in a sample without the test compound indicates the compound is not a candidate to treat mitochondrial dysfunction by reducing OMA1 protease activity.

In one aspect of the invention provides methods of identifying compounds which decrease or inhibit OMA1 activity and thereby are effective in treating diseases resulting from OMA1 mediated mitochondrial dysfunction. In another aspect of the invention, conditions or compounds which increase OMA1 activity may be identified indication stimuli which contribute to mitochondrial dysfunction. In some embodiment, the biological samples may be pretreated with known activators or inhibitors of OMA1 prior to providing a test compound. In one aspect, identification is performed in a cell free system. In another aspect, the identification is performed using a biological sample. In a non-limiting example, the sample is a culture of cells, cultured in vitro containing the reporter of the invention. In this system the method of the invention includes providing a cell a reporter molecule including a detection domain linked to a linker domain comprising an OMA1 cleavage site and a repressor domain operably linked to the linker domain and represses the signal of the detection domain. Cleavage at the OMA1 cleavage site increases the signal of the detection domain. The cell is then contacted with a compound under conditions sufficient for the compound to interact. The activity of the detection domain is then measured.

A decrease in the activity of the detection domain indicates an ability of the compound to inhibit OMA1. An increase in the activity of the detection domain indicates an ability of a compound or condition to activate OMA1. In general a "decrease" is a reduction in activity of the reporter molecule by at least 10%, at least 20%, at least 30% as compared to a control cell not contacted with the compound. Likewise, an "increase" is an induction of the reporter molecule by at least 10%, at least 20%, at least 30%, as compared to a control cell not contacted with the compound.

The method comprises contacting the one or more biological samples with a reporter molecule and a test compound. The test compound may be chosen from a library of compounds. Suitable compounds include small molecules, pharmaceutically active compounds (i.e., drugs), natural products, carbohydrates, lipid molecules, amino acid derivatives, peptides, peptide mimetics, nucleic acids, antisense oligonucleotides, microRNAs, and so forth. In exemplary embodiments, the test compound is selected from a library of small molecules. In general, a small molecule is defined as a molecule having a molecular weight of less than about 1000 daltons (Da). In other embodiments, the plurality of compounds may comprise larger molecules that are cell permeable.

Libraries of small molecules are available through repositories or commercial sources, and means for generating libraries of small molecules are well known in the art. Exemplary small molecule compounds include those that may affect OMA1 activity, mitochondrial fission or fusion, cell cycle control proteins, replication control proteins, chromatin remodeling proteins, mitotic control proteins, cell division control proteins, signal transduction pathways, membrane receptors, receptor tyrosine kinases, intracellular kinases, phosphatases, and other enzymes.

The compounds to be screened generally will be dissolved in a suitable solvent (such as, e.g., DMSO or ethanol) and added to the medium containing the biological sample. The test compounds may be distributed to the wells of a multi-well system using multichannel pipette systems or robotic liquid handling systems. Initially, the biological sample will be contacted with a single concentration of each compound. If the initial concentration of a compound is toxic to the biological sample, then that compound will be retested at a lower concentration. Additionally, compounds that affect the signal of the reporter molecule will be rescreened at several different concentrations to determine the half maximal effective concentration (EC50). For statistical purposes, contact with a compound of interest will be performed in at least duplicate or triplicate.

During each screening procedure, a percentage of biological samples comprising a reporter molecule will serve as untreated controls. That is, the untreated biological sample will not be contacted with any compounds of interest but rather will be contacted only with the solvent used to dissolve the compounds of interest.

All suitable methods for detecting and measuring the detection domain of the reporter molecules known to one of skill in the art are contemplated within the scope of the invention. For example, epitope binding agent assays (i.e. antibody assays), enzymatic assays, electrophoresis, chromatography and/or mass spectrometry may be used. Non-limiting examples of epitope binding agent assays include an ELISA, a lateral flow assay, a sandwich immunoassay, a radioimmunoassay, an immunoblot or Western blot, flow cytometry, immunohistochemistry, and an array. In one embodiment, ceramides are detected using mass spectrometry. The reporter molecule may be monitored visually by microscope or by using a variety of detection/image capture devices. Non-limiting examples of suitable detection/image capture devices include cameras, imaging systems, plate readers, or camera-mounted microscope systems. The detection/image capture device may utilize visible light, fluorescent light, IR light, or uv light. The light may illuminate the multi-well system from the top, bottom, or side. The detection/image capture device may be coupled to image processing systems, image analysis systems (e.g., systems that automatically score for the desired phenotype from the captured images), and/or digital storage systems. In exemplary embodiments, the detection/image capture system is capable of taking high resolution images that can be digitally zoomed to analyze subregions of the image. For example, a high content, high resolution image of a multi-well system can be digitally zoomed to analyze oocytes or embryos in individual wells of the system.

In some embodiments, the monitoring step may comprise time-lapse image capture. For example, high content digital images may be taken at regular intervals, e.g., intervals of 2, 5, 10, 15, 20, 25, 30, 45, or 60 minutes. The total duration of time-lapse image capture will depend upon the samples that are monitored. Additionally, more than one multi-well system can be concurrently monitored by placing the multi-well systems on a rotating stage or platform. For example, two, three, four, five, or more multi-well systems may be placed on the rotating stage/platform, wherein the stage/platform can be automatically rotated and images can be automatically acquired at regular intervals. In other embodiments, the monitoring step may comprise end-point image capture.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

As various changes could be made in the above-described reporter molecules and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to the Examples

Mitochondria are dynamic organelles that continuously undergo two opposing processes, fission and fusion, to maintain normal mitochondrial function (1-4). Impaired mitochondrial function has been linked to numerous pathologies, including neurodegenerative (5), cardiovascular (6, 7), and metabolic diseases (1). During stressful conditions, mitochondrial fusion allows compensatory mixing of functional mitochondrial content with damaged mitochondria, thereby mitigating acute injury. Thus, disrupted fusion can exacerbate acute damage and lead to irreversible loss of respiratory capacity and subsequent cell death (4, 8-11). A key regulator in mitochondrial fusion is the optic atrophy protein termed OPA1 (9, 12). Fusion-competent OPA1 requires both the long and short forms and studies show that loss of the long form (L-OPA1) leads to impaired fusion. OPA1 is cleaved to its short form (S-OPA1) by two zinc metalloproteinases, OMA1 and YME1L (12-14), which are located in the mitochondrial inner membrane. OMA1 is an ATP-independent protease with activities overlapping with the m-AAA protease. Studies show that OMA1 is a stress-induced protease, whereas YME1L, an ATP-dependent protease, is thought to be constitutively active and is required for normal mitochondrial function as demonstrated by its knockout lethality (14-16). Conversely, over-active OMA1 is pathogenic (17-20), presumably by disrupting OMA1-mediated mitochondrial fusion.

Interestingly, OMA1-deficient mice exhibit protection from neurodegeneration (18), renal ischemia (19), and heart failure (20) which strongly suggest that OMA1 is a promising therapeutic target. However, the lack of quantitative assays that directly measures OMA1 activity is a serious impediment to characterization of OMA1's function during disease. The current gold standard for qualitatively characterizing assessing OMA1 activity is via western blot analysis of OPA1 cleavage from long to short form which is not quantitative, and where specificity is typically inferred. The loss of expression in the long form of OPA1 suggests activation of OMA1 during cell stress, but only via indirect inference.

Figure 1B:
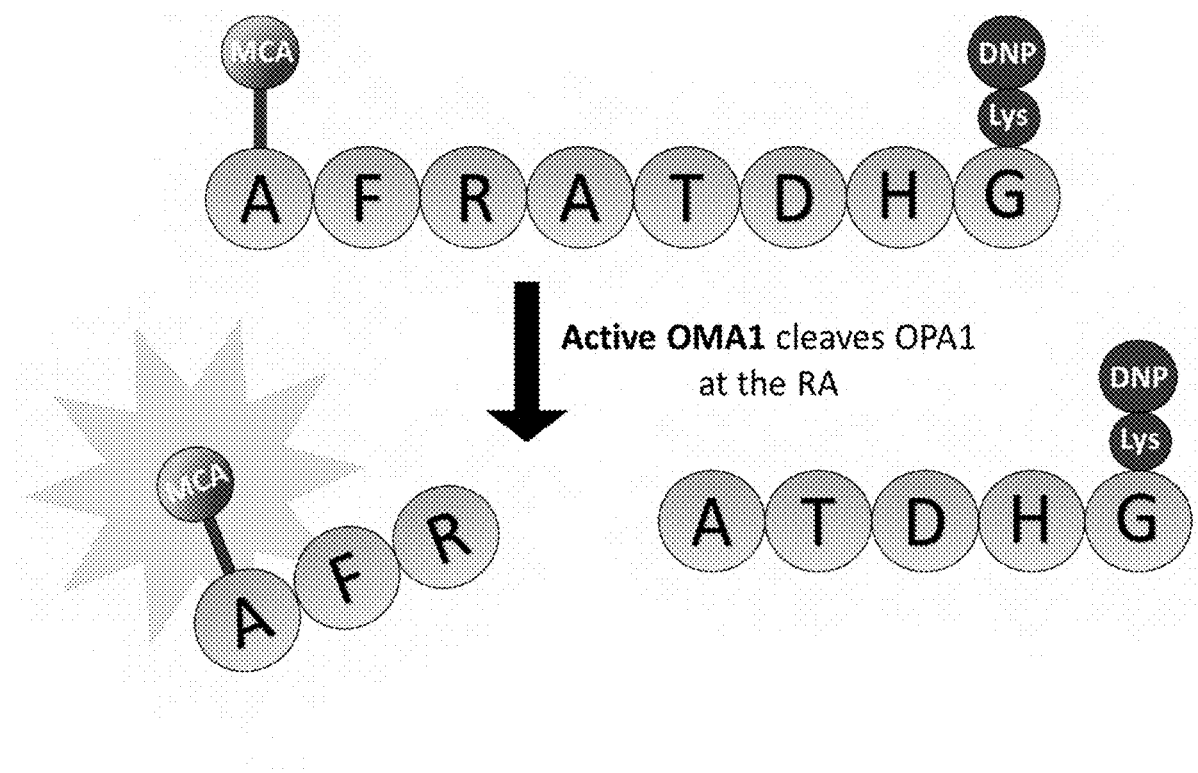

The present disclosure provides a method which utilizes fluorescent resonance emission technology (FRET) for directly measuring OMA1 activity. The assay is based, in-part, on showing that OMA1 cleaves OPA1 between the 194 Arginine (R) and 195 Alanine (A) residues, also described as the S1 site (12). Using this (OPA1) 51 cleavage site sequence, an eight amino acid peptide (MCA-AFRAT-DHG-DNP) was synthesized, with an MCA (7-Methoxycoumarin-4-ylacetyl) fluorophore moiety on the N-terminus and a DNP (2,4-Dinitrophenyl) quencher moiety on the C-terminus. This OPA1 FRET substrate has very low intrinsic fluorescence due to the proximity of the DNP quencher group; once cleaved, the quenching is relieved, and free MCA fluorescence, and the resulting fluorescence is then measured spectrofluorometrically using a plate reader (FIG. 1B).

Example 1: Indirect Measurement of OMA1 Activity

The stress activated protease, OMA1, is a zinc metalloproteinase known to cleave the mitochondrial fusion protein OPA1 into long and short isoforms. Excessive OPA1 processing by OMA1 promotes mitochondrial fragmentation and, if persistent, triggers cell death and tissue degeneration. Current methods used to assay OMA1 activity rely on an indirect measure through detection of OPA1 processing. As can be seen in FIG. 1A, under control conditions OPA1 appears as two distinct bands, long and short isoforms, by western blotting. In contrast, under stressed conditions OPA1 is appears as one distinct band, an indication of processing into primarily the short isoform of OPA1. The fact that OPA1 can be processed by multiple proteases complicates the current method of assaying OMA1 activity, whereas the present invention provides direct, efficient measure of OMA1 activity (FIG. 1B).

Example 2: Kinetics and Specificity of the OMA1 Reporter Assay

Figure 2A:
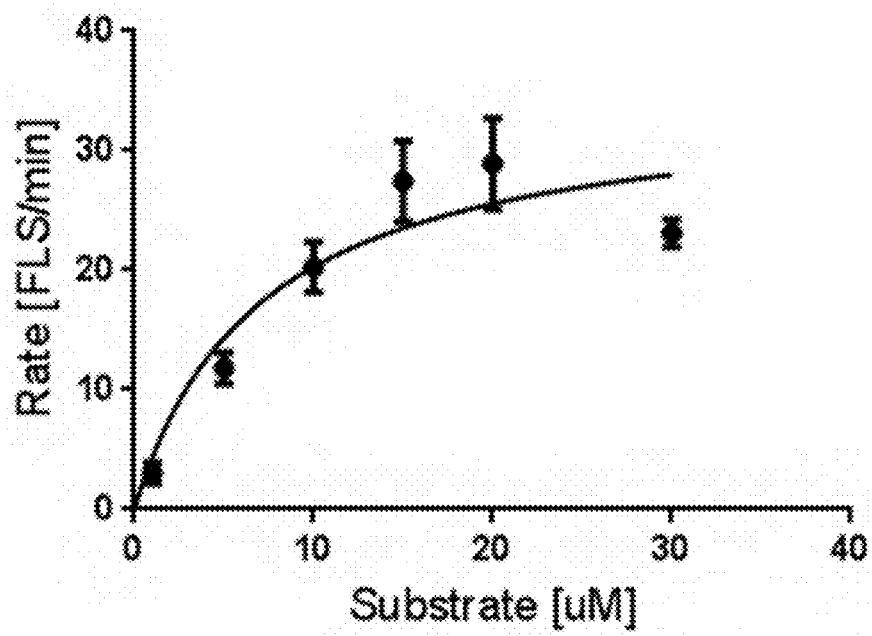
FIG. 2A and FIG. 2B show the kinetic parameters of OMA1 activity assay

Michaelis-Menten kinetics was used to determine the Km and Vmax for cleavage of the OPA1 FRET substrate. Six concentrations (1, 5, 10, 15, 20, and 30 μM) of the OPA1 FRET substrate were evaluated using untreated NRK cell lysates (5 μg) in the activity assay (FIG. 2A). The Vmax was calculated to be 34.6 FLS/min and the Km 7.1 μM. Next, we selected 5 μM of the OPA1 FRET substrate in the OMA1 activity assay to ensure we have a sensitive assay when using a relatively small amount of NRK cell lysate (5 μg).

Figure 2B:
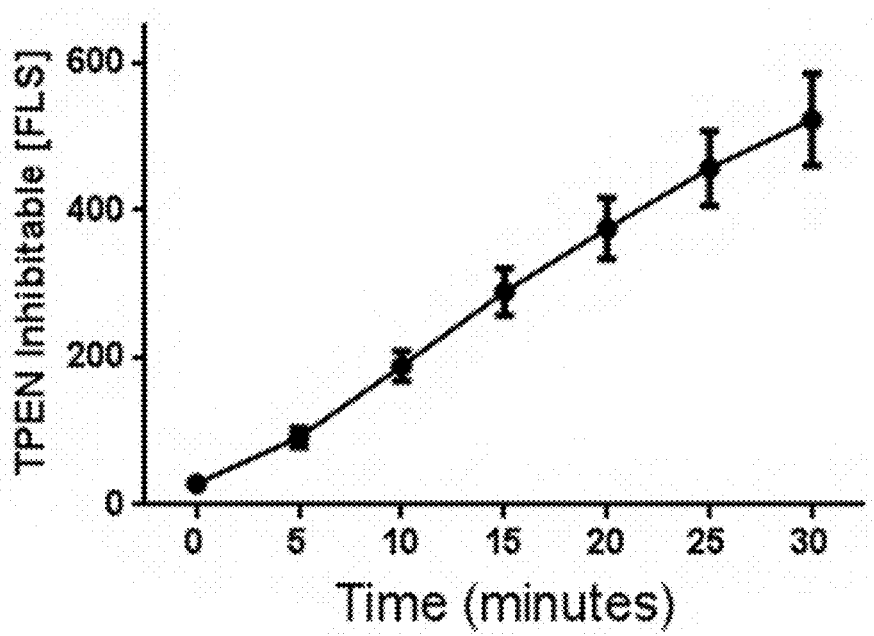

It is preferable to use a substrate concentration at least double its Km value to avoid rate changes due to substrate depletion. However, the linear response over the 30 min reaction period (FIG. 2B) strongly indicates that substrate depletion is negligible during this time—not surprising given the small amounts of OMA1 enzyme present in the lysate aliquots.

Figure 3A:
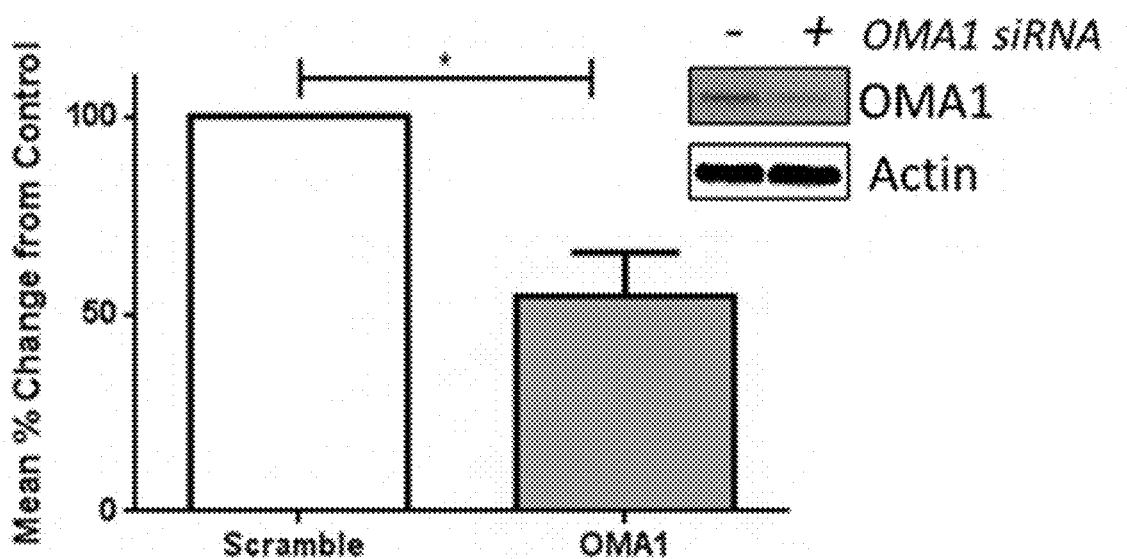
FIG. 3A and FIG. 3B depict the assay has specificity towards OMA1, but not YME1L, mediated OPA1 cleavage.
Figure 3B:
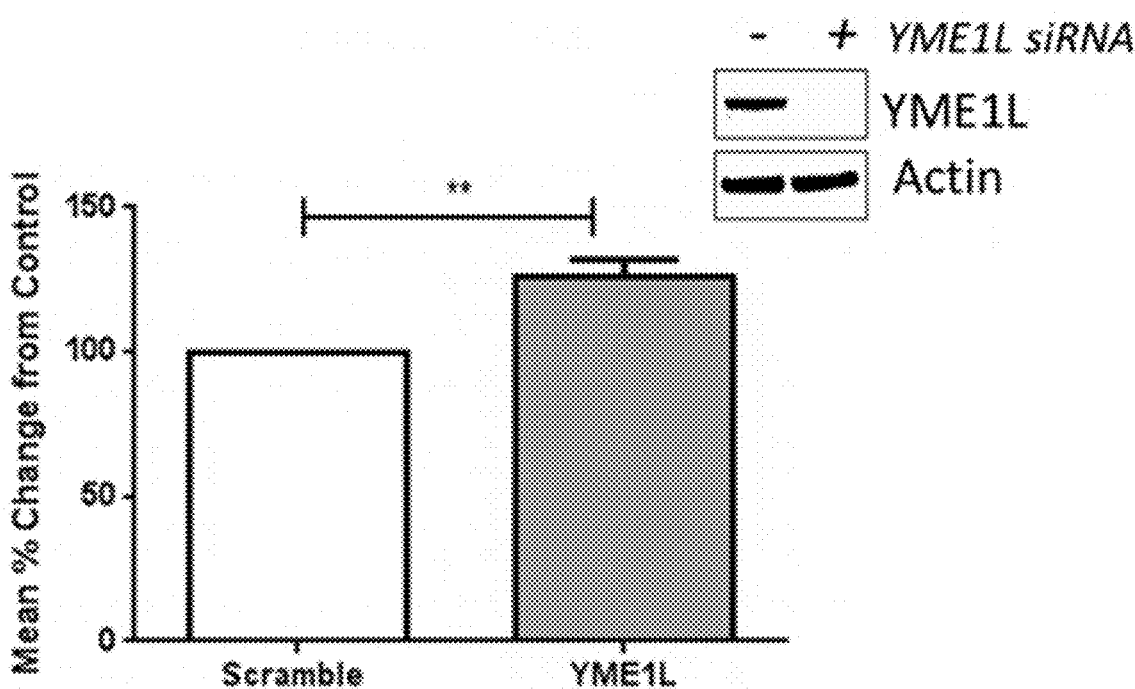

Next, it was evaluated whether knockdown of OMA1 in NRK cells reduced apparent activity in the new assay. Protein lysates harvested from OMA1 siRNA-treated (50 nM; 24 hr) NRK cells showed a 45% reduction of fluorescence/min (slope of OMA1 activity) compared to control cells exposed to a scrambled siRNA. This reduction in activity is consistent with the extent of lowered OMA1 expression (FIG. 3A inset). Interestingly, cells treated with YME1L siRNA (50 nM; 24 hr) showed a significant increase (**p=0.003) in OMA1 activity compared to scramble siRNA (FIG. 3B). A potential explanation for increase in OMA1 activity in NRK cells treated with YME1L siRNA is that YME1L has been shown to degrade OMA1 (14, 21). In addition, it has been shown that loss of YME1L may act as a cellular stressor leading to increased OMA1 activity (22). Western blots confirmed knockdown of OMA1 and YME1L after transfection with siRNA at the respective time points (24 hr for OMA1 and 24 hr for YME1L) (FIGS. 3A and B insets). Clearly, the knockdown of OMA1 after 24 hr of siRNA transfection was not 100%, which provides an explanation for the ~45% reduction in OMA1 activity. Higher concentrations of OMA1 siRNA or longer time points post transfection did not improve OMA1 knockdown efficiency (data not shown). It is possible that a stable transfection protocol would yield greater knockdown; however, the purpose of these studies was to show that our activity assay modulates with OMA1 knockdown. Taken together, these findings provide strong evidence that the observed protease activity in NRK cell lysates emanates from OMA1 and not YME1L. This was not unexpected, since the peptide sequence 'AFRATDHG' is specific for the OMA1-dependent OPA1 cleavage site (Site 1), and not the site where YME1L cleaves. The precise site within OPA1 that YME1L cleaves, which is referred to as Site 2, has not been established but it does not overlap and is clearly different than the OMA1 site (12).

The eight amino acid OPA1 FRET substrate (AFRATDHG)(SEQ ID NO:1) used in the OMA1 activity assay was derived from the rat OPA1 protein sequence (residues 192-199). According to Ishihara, the OMA1-dependent OPA1 processing has been reported to occur between the 194 Arginine (R) and the 195 Alanine (A) residues (12). To test whether the R-A sequence is critical for measuring OMA1 activity in our assay, we synthesized an eight amino acid FRET peptide (ATDHGSES)(SEQ ID NO:34) based on a the OPA1 sequence, but downstream of the cleavage site, and thus not containing the R-A sequence (Table 1). The absence of the "R" residue within the original OPA1 FRET substrate (AFRATDHG)(SEQ ID NO:1) abolished fluorescence indicating that the "R" residue is essential for detecting OMA1 activity. Further studies are underway to determine the minimal binding site required for detection of OMA1 activity.

TABLE 1

RA sequence is essential for OPA1 FRET substrate recognition.

| FRET Substrate MCA-XXXXX-Lys DNP | OMA1 Activity |
|---|---|
| AFRATDHG (confirmed sequence) (SEQ ID NO: 1) | 100% |
| ATDHGSES (no RA motif) (SEQ ID NO: 34) (AFRATDHGSES) | 2.71% |

OMA1 activity was calculated as an average slope over 30 min compared to AFRATDHG substrate. The 'no RA' sequence was calculated as a percent difference from the confirmed sequence; n = 3.

Example 3: TPEN Inhibits OMA1 Activity

Figure 4:
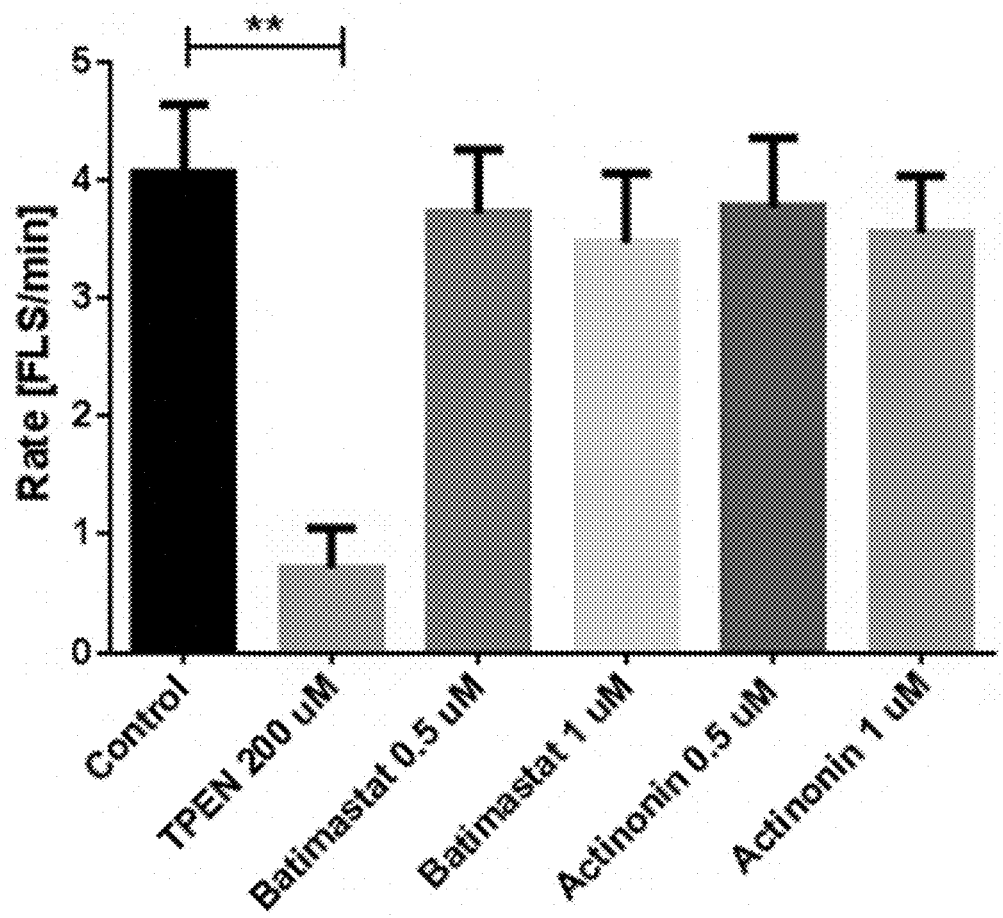
FIG. 4 shows TPEN inhibits OMA1 activity. NRK cell lysates were incubated with TPEN, Actinonin, or Batimastat and the designated concentrations. Only TPEN reduced OMA1 activity measured as slope (FLS/min), compared to untreated NRK cell lysates, **p=0.003. One-way ANOVA followed by Dunnett's multiple comparisons test was used. Data is expressed as mean±SEM; n=4.

OMA1 belongs to a unique subset of proteases in that it is zinc dependent and ATP independent. TPEN is more specific for chelating zinc, and was therefore used in the OMA1 activity assay as an inhibitor. The classical OMA1 inhibitor, o-phenanthroline (12, 23), has less metal specificity and has intrinsic fluorescence that interfered with the FRET assay. TPEN dramatically decreased fluorescence (p=0.003**) compared to control NRK cell lysates not containing TPEN, illustrating that zinc is necessary for the activity seen (FIG. 4). To further establish the specificity of our new OMA1 activity assay we wanted to test whether classic zinc metalloproteinase (MMP) inhibitors could inhibit OMA1 activity. We found that neither the broad-spectrum MMP inhibitor, batimastat (0.5-1 µM), or the meprin A inhibitor, actinonin (0.5-1 µM), altered OMA1 activity (measured as slope=FLS/min) showing that our activity assay has high specificity towards OMA1 (FIG. 4)—a non-classic MMP. It is important to note that prior studies have reported that aspartic protease inhibitors (e.g. pepstatin A), cysteine protease inhibitors (e.g. E64D) and pefabloc/TPCK serine protease inhibitor (e.g. pefabloc/TPCK) do not prevent OMA1-dependent OPA1 cleavage (12, 24). This is consistent with our data since NRK cells are lysed with RIPA lysis buffer containing numerous protease inhibitors (including cysteine, serine, aspartic, trypsin-like inhibitors-all present in HALT cocktail), yet we still see OMA1 activity.

Much of our knowledge of the function and activation of OMA1 is based on OMA1 knockout cell, yeast, and mouse models in evaluating the functional role of OMA1 (18, 19, 25-28). These are informative proof-of-concept experiments that have established the critical role of OMA1 in helping regulate mitochondrial quality control. However, further advancements in understanding the role of OMA1 and its potential as a therapeutic target are dependent on a specific and semi-quantitative activity measurement.

This is the first study to demonstrate the feasibility of a fast and inexpensive assay to measure OMA1 activity using a FRET based high throughput assay. This study should accelerate our understanding of the role OMA1 plays in both normal and abnormal pathology, and the conditions under which it is induced and inactivated. The OMA1 activity assay may provide a new tool for researchers to further explore the role of OMA1 in their model systems and to identify new drug targets to treat diseases involving over activation of OMA1.

Example 4: Use of the Reporter to Detect Mitochondrial Dysfunction

Figure 5:
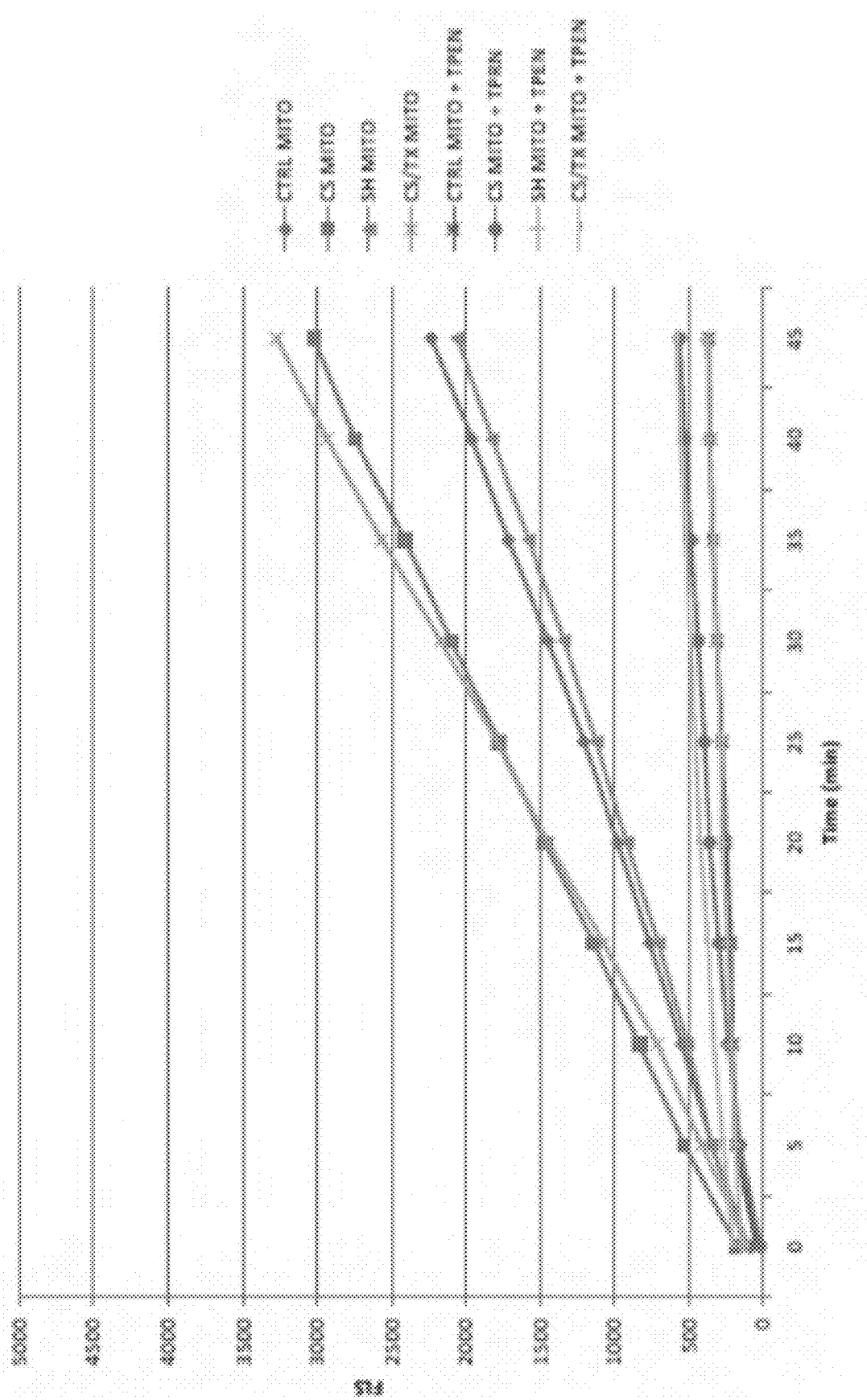
FIG. 5 shows increased OMA1 activity in mitochondria after renal cold storage and transplantation. OMA1 activity of rat renal mitochondrial lysates shows that cold storage alone or followed by renal transplant increases OMA1 activity compared to control or sham lysates. TPEN effectively inhibits FLS increase.
Figure 6A:
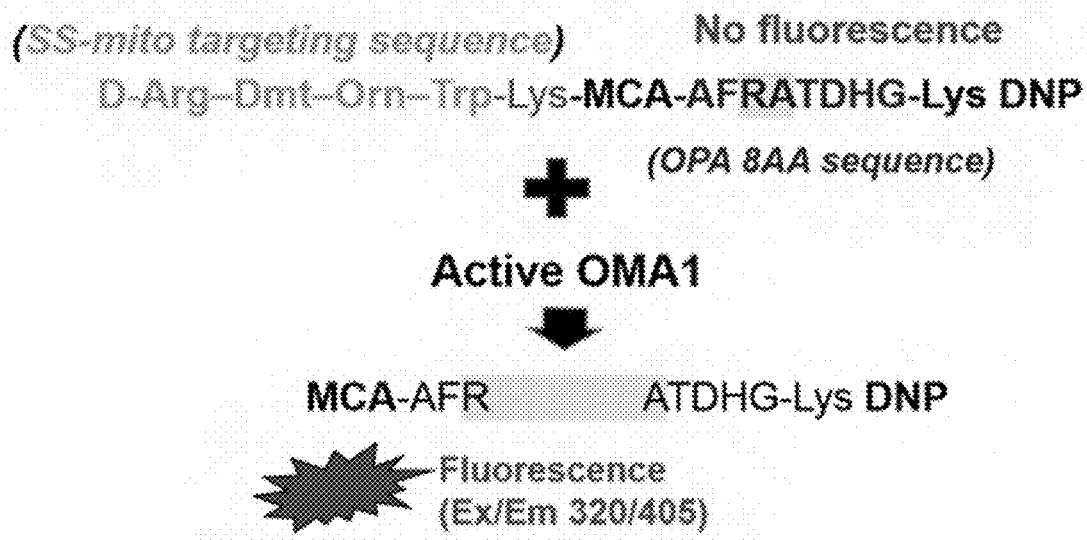
FIG. 6A and FIG. 6B show the development of a novel live-cell OMA1 activity assay.
Figure 6B:
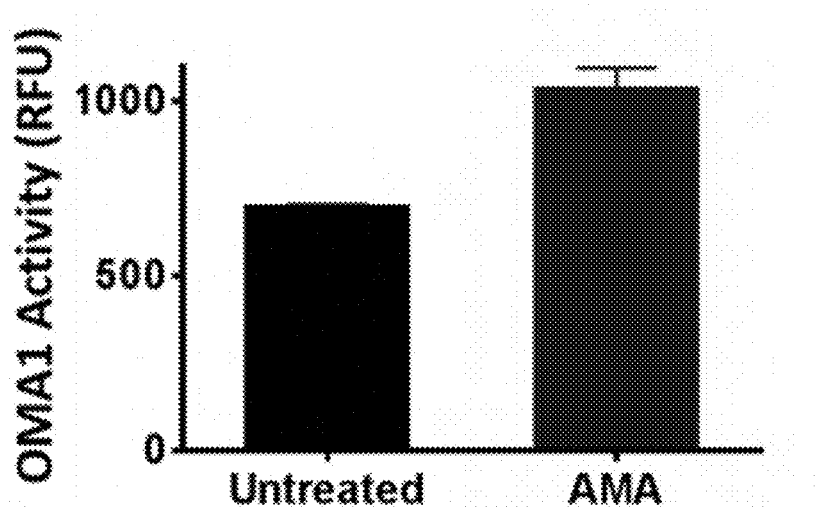

Long-term renal function is compromised in patients receiving deceased donor kidneys which require cold storage exposure prior to transplantation. It is established that extended cold storage plus transplantation of kidneys induces renal mitochondrial dysfunction. To assay OMA1 activity under stress conditions known to induce mitochondrial dysfunction an exemplary reporter molecule of the invention was employed in mitochondrial lysates from control kidneys (CTRL), sham surgery (SH), cold storage alone (CS), or cold storage and transplantation (CS/TX) conditions. FIG. 5 shows increased an increase in OMA1 activity under CS and CS/TX conditions when compared to CTRL and SH conditions. Moreover, the addition of TPEN effectively inhibits the reporter molecule activation.

Materials and Methods for Examples 1-4

Cell Model:

Normal rat kidney cells (NRK-52E; ATCC No. CRL-1571) were maintained in a humidified incubator with 5% CO2, 95% air at 37° C. in DMEM containing 5% fetal bovine serum. Renal cell lysates from normal rat kidney (NRK) epithelial cell line were prepared by using radioimmunoprecipitation assay (RIPA) buffer (Pierce) with 1 mM PMSF (Sigma), 1.2 mM Na3VO4 (Sigma), 2.5 mM NaF (Sigma), 1 mM DTT (Sigma), 1× of Halt Protease & Phosphatase inhibitor cocktail (Thermo Scientific), and 5 mM EDTA (Thermo Scientific). Protein concentrations were determined by Coomassie Plus Protein Assay Reagent (Pierce).

OMA1 and YME1L siRNA Knockdown in NRK Cells.

50 nM OMA1 siRNA (siGENOME SMARTpool, Dharmacon) and 50 nM YME1L siRNA (Ambion) were used to knockdown OMA1 and YME1L in NRK cells, respectively. Scrambled siRNA (ON-TARGETplus Control Pool, Non-Targeting Pool, Dharmacon) was used as a control. SiRNA was diluted (50 nM final concentration) in OptiMEM 1× (Life Technologies) with Lipofectamine RNAiMAX (Invitrogen) accordingly to manufacturer's instructions. At 50% cell confluency, NRK cells were transfected with the siRNA solution, and lysed 24 hr later using RIPA lysis buffer. Successful knockdown of OMA1 and YME1L was confirmed via protein immunoblotting.

Western Blot Analysis.

NRK cell lysates (25 µg) were resolved on Bolt 4-12% Bis-Tris Plus SDS precast gels (Invitrogen) and then transferred to PVDF membrane. Western blot analysis was performed using antibodies against proteins: YME1L (1:1000 in T/TBS, Abgent, #AP4882a); OMA1 (1:500 in 5% BSA, Santa Cruz, # sc-515788); and β-actin (1:1000, Sigma, # A5441). Actin served as the loading control for all western blot experiments. Probed membranes were washed three times T/TBS and immune-reactive proteins were detected using horseradish peroxidase conjugated secondary antibodies (1:30000 dilution) (Seracare KPL, USA) and enhanced chemiluminescence (Thermoscientific, USA).

OMA1 Activity Assay.

Our OMA1 activity assay utilizes an 8-mer peptide derived from the cleavage sequence of OPA1, which is reported to be specific of OMA1 which is referred as the OPA1 FRET substrate. The peptide contains a fluorogenic MCA moiety on the N-terminus and a DNP quencher moiety on the C-terminus (FIG. 1), which was custom-synthesized by LifeTein LLC and handled accordingly to the manufacturer's instructions. Using a final 100 µl reaction volume and black, opaque 96 well plates (Costar), the reagents were added in the following order: 1) OMA1 activity assay buffer (50 mM of Tris/HCl, pH=7.5, 40 mM of KCl), 2) 5 µg of protein sample, 3)+/−200 µM of the zinc chelator N,N,N', N'-Tetrakis (2-pyridylmethyl)ethylenediamine (TPEN) resuspended in 100% ethanol and lastly, 4) the OPA1 FRET substrate (5 µM final concentration; dissolved in DMSO). Fluorescence was recorded (excitation/emission of 320/405 nm) once per minute for 30 min at 37° C. using a fluorescent plate reader (SpectraMax M2e, Molecular Devices equipped with SoftMax Pro v5 software).

For the statistical analysis, the average fluorescence of the OPA1 FRET substrate alone was measured (<150 relative FLS units) and that value was subtracted from the sample values. The values were reported as a difference of TPEN inhibition [(sample X)−(sample X+TPEN)] where the slopes between 0-30 min were calculated (by linear regression) and each treatment were compared to appropriate controls. Thus, OMA1 activity was calculated by subtracting TPEN-inhibitable fluorescence from total fluorescence to enhance specificity.

Statistical Analysis. Results are presented as mean±standard error of the mean (S.E.M.) using Graph Pad Prism 7 software. At least 3-4 independent biological samples were carried out for each experiment and treatment, with three replicates of each individual sample. Km (substrate concentration that causes half-maximal enzyme velocity) and Vmax (maximum velocity extrapolated to infinite substrate concentration) were analyzed using Michaelis-Menten (nonlinear regression) built-in analysis in Graph Pad Prism 7. Depending on number of conditions, either a one-way ANOVA followed by a Dunnett's post-hoc test or an unpaired students t-test were performed (unless otherwise stated). All differences were judged to be significant at $P<0.05$.

Example 5: OMA1 Substrate Specificity

As described above, disruption of the 'RA motif' within the original FRET substrate peptide (AFRATDHG)(SEQ ID NO:1) abolished fluorescence indicating that this motif is required for activity (Table 1). Interestingly, when the Arginine-Alanine (RA) motif was flanked by alanine residues (AARAAAAA)(SEQ ID NO: 26), OMA1 activity was notably decreased by 65% compared to the standard substrate sequence (Table 2, #3), suggesting the importance of the flanking sequences. Changing the Arg to Lys reduced activity by ~40% (Table 2, #4). Table 2 shows the summary of using modified 8-mer sequences between the FRET moieties with regard to OMA1 activity (shown as % comparison to AFRATDHG (SEQ ID NO:1), representative of 2-3 experiments/substrate). OMA1 activity was calculated as slope over 30 min compared to AFRATDHG (SEQ ID NO:1).

TABLE 2

| FRET Substrate MCA-XXXXX-Lys DNP | OMA1 Activity |
|---|---|
| 1. AFRATDHG (confirmed sequence) (SEQ ID NO: 1) | 100% |
| 2. ATDHGSES (no RA motif) (SEQ ID NO: 34) (AFRATDHGSES) | 2.71% |
| 3. AARAAAAA (only RA) (SEQ ID NO: 26) | 35% |
| 4. AFKATDHG (R to K) (SEQ ID NO: 27) | 61% |

Is there an OMA1 substrate specificity sequence? Other than OPA1, the only other well-characterized OMA1 substrate is the protease YME1L. Since the data confirms the 'RA' motif as the cleavage site recognized by OMA1, we searched NCBI protein databases (rat YME1L sequence) for 'RA' and found three regions within YME1L containing 'RA', which will be used in our FRET based assay to measure OMA1 cleavage of YME1L. The inventors recent work using a rat kidney transplantation injury model revealed that the expression of several mitochondrial proteins were diminished following transplantation, which was hypothesized to be due to 'over-active' OMA1. These proteins included other regulators of mitochondrial fusion: OPA1, YME1L, Mitofusin 1 and 2, and mitochondrial fission factor 1. When these proteins were searched using the rat protein sequence database, it was found that all contained a 'RA' motif. Conversely, the expression of two mitochondrial proteins (MnSOD and Core 2) which do not change after transplantation do not have the 'RA' motif. In addition, unpublished data show reduced expression of mitochondrial respiratory complex proteins (SDHA-in complex II and NDUFS3-in complex I) after transplantation; these proteins also contain the 'RA' motif. Two other important mitochondrial proteins-aconitase and cytochrome c also show the 'RA' motif; further studies will determine using our cell injury models if these proteins might also be previously unreported substrates for OMA1. Obviously, cleavage of these important mitochondrial regulators could lead to disrupted mitochondrial function and possibly cell/organ damage. It is reasonable to expect that that the flanking sequences (either side of 'RA') would alter OMA1 binding affinity, and therefore create a rank order of substrate preference, meaning that some would be cleaved earlier and more completely than others. Substrate peptides based on these sequences will help answer that question, as well as potentially refining the OMA1 assay, and providing starting points for other inhibitor structures.

Example 6: Novel OMA1 Live-Cell Assay

Live-Cell OMA1 activity assay: To deliver the FRET OMA1 peptide to mitochondria in living cells, we utilized a modified short Szeto-Schiller (SS) peptide sequence1 attached to the amino terminus of the 8 amino acid FRET sequence (custom synthesized by LifeTein) (FIG. 5A). Cells will be plated on black 96 well plate loaded with peptide (~4 hr; 37° C.) followed by exposure to the mitochondrial stressor, AMA, which we have shown induces OMA1 activity (FIG. 5B). Small molecule/peptide library subsets or novel peptides will be screened for inhibitory activity using this live-cell OMA1 assay.

Live-cell OMA1 activity assay preliminary results: To deliver the FRET peptide to mitochondria in living cells, we have used a modified short Szeto-Schiller (SS) mitochondrial targeting peptide sequence1 (d-arginine, dimethyl tyrosine, ornithine, tryptophan) attached to the amino terminus of the eight amino acid FRET sequence (FIG. 5A). Normal rat kidney (NRK-52E; ATCC No. CRL-1571) cells were plated on black 96-well cell culture plates (10,000 cells/well). The next day, the cell permeable peptide was added to cells (10 µM; 4 hr; 37° C.) followed by exposure to ATP depletion/antimycin A (50 nM; 30 min) and OMA1 activity measured (ex/em 320/405) using a plate reader. Our early studies show that ATP depletion increased OMA1 activity (fluorescence) in live cells using our newly developed live-cell OMA1 activity assay (FIG. 5B). Future studies will optimize the mitochondrial targeting sequence so that the highest efficiency of mitochondrial localaization without altering mitochondrial oxidant levels will be achieved, which we predict will yield the highest sensitivity for the live-cell OMA1 activity assay.

REFERENCES

1. Wai T, Langer T. Mitochondrial Dynamics and Metabolic Regulation. Trends Endocrinol Metab. 2016; 27(2):105-17.
2. Anand R, Langer T, Baker M J. Proteolytic control of mitochondrial function and morphogenesis. Biochim Biophys Acta. 2013; 1833(1):195-204.
3. Leonard A P, Cameron R B, Speiser J L, Wolf B J, Peterson Y K, Schnellmann R G, et al. Quantitative analysis of mitochondrial morphology and membrane potential in living cells using high-content imaging, machine learning, and morphological binning. Biochim Biophys Acta. 2015; 1853(2):348-60.
4. Mishra P, Varuzhanyan G, Pham A H, Chan D C. Mitochondrial Dynamics is a Distinguishing Feature of Skeletal Muscle Fiber Types and Regulates Organellar Compartmentalization. Cell Metab. 2015; 22(6):1033-44.
5. Chen H, Chan D C. Mitochondrial dynamics—fusion, fission, movement, and mitophagy—in neurodegenerative diseases. Hum Mol Genet. 2009; 18(R2):R169-76.
6. Vasquez-Trincado C, Garcia-Carvajal I, Pennanen C, Parra V, Hill J A, Rothermel B A, et al. Mitochondrial dynamics, mitophagy and cardiovascular disease. J Physiol. 2016; 594(3):509-25.
7. Ong S B, Hall A R, Hausenloy D J. Mitochondrial dynamics in cardiovascular health and disease. Antioxid Redox Signal. 2013; 19(4):400-14.
8. Olichon A, Baricault L, Gas N, Guillou E, Valette A, Belenguer P, et al. Loss of OPA1 perturbates the mitochondrial inner membrane structure and integrity, leading to cytochrome c release and apoptosis. J Biol Chem. 2003; 278(10):7743-6.
9. Olichon A, Guillou E, Delettre C, Landes T, Arnaune-Pelloquin L, Emorine L J, et al. Mitochondrial dynamics and disease, OPA1. Biochim Biophys Acta. 2006; 1763 (5-6):500-9.
10. Mishra P, Carelli V, Manfredi G, Chan D C. Proteolytic cleavage of Opa1 stimulates mitochondrial inner membrane fusion and couples fusion to oxidative phosphorylation. Cell Metab. 2014; 19(4):630-41.
11. Rainbolt T K, Saunders J M, Wiseman R L. YME1L degradation reduces mitochondrial proteolytic capacity during oxidative stress. EMBO Rep. 2015; 16(1):97-106.
12. Ishihara N, Fujita Y, Oka T, Mihara K. Regulation of mitochondrial morphology through proteolytic cleavage of OPA1. EMBO J. 2006; 25(13):2966-77.
13. Head B, Griparic L, Amiri M, Gandre-Babbe S, van der Bliek A M. Inducible proteolytic inactivation of OPA1 mediated by the OMA1 protease in mammalian cells. J Cell Biol. 2009; 187(7):959-66.
14. Anand R, Wai T, Baker M J, Kladt N, Schauss A C, Rugarli E, et al. The i-AAA protease YME1L and OMA1 cleave OPA1 to balance mitochondrial fusion and fission. J Cell Biol. 2014; 204(6):919-29.
15. Zhang K, Li H, Song Z. Membrane depolarization activates the mitochondrial protease OMA1 by stimulating self-cleavage. EMBO Rep. 2014; 15(5):576-85.
16. Wai T, Garcia-Prieto J, Baker M J, Merkwirth C, Benit P, Rustin P, et al. Imbalanced OPA1 processing and mitochondrial fragmentation cause heart failure in mice. Science. 2015; 350(6265):aad0116.
17. Parajuli N, Shrum S, Tobacyk J, Harb A, Arthur J M, MacMillan-Crow L A. Renal cold storage followed by transplantation impairs expression of key mitochondrial fission and fusion proteins. PLoS One. 2017; 12(10): e0185542.
18. Korwitz A, Merkwirth C, Richter-Dennerlein R, Troder S E, Sprenger H G, Quiros P M, et al. Loss of OMA1 delays neurodegeneration by preventing stress-induced OPA1 processing in mitochondria. J Cell Biol. 2016; 212(2):157-66.
19. Xiao X, Hu Y, Quiros P M, Wei Q, Lopez-Otin C, Dong Z. OMA1 mediates OPA1 proteolysis and mitochondrial fragmentation in experimental models of ischemic kidney injury. Am J Physiol Renal Physiol. 2014; 306(11):F1318-26.
20. Acin-Perez R, Lechuga-Vieco A V, Del Mar Munoz M, Nieto-Arellano R, Torroja C, Sanchez-Cabo F, et al. Ablation of the stress protease OMA1 protects against heart failure in mice. Sci Transl Med. 2018; 10(434).
21. Rainbolt T K, Lebeau J, Puchades C, Wiseman R L. Reciprocal Degradation of YME1L and OMA1 Adapts Mitochondrial Proteolytic Activity during Stress. Cell Rep. 2016; 14(9):2041-9.
22. Ruan Y, Li H, Zhang K, Jian F, Tang J, Song Z. Loss of Yme1L perturbates mitochondrial dynamics. Cell Death Dis. 2013; 4:e896.
23. Kaser M, Kambacheld M, Kisters-Woike B, Langer T. Oma1, a novel membrane-bound metallopeptidase in mitochondria with activities overlapping with the m-AAA protease. J Biol Chem. 2003; 278(47):46414-23.
24. Baker M J, Lampe P A, Stojanovski D, Korwitz A, Anand R, Tatsuta T, et al. Stress-induced OMA1 activation and autocatalytic turnover regulate OPA1-dependent mitochondrial dynamics. EMBO J. 2014; 33(6):578-93.
25. Quiros P M, Ramsay A J, Sala D, Fernandez-Vizarra E, Rodriguez F, Peinado J R, et al. Loss of mitochondrial protease OMA1 alters processing of the GTPase OPA1 and causes obesity and defective thermogenesis in mice. EMBO J. 2012; 31(9):2117-33.
26. Kong B, Wang Q, Fung E, Xue K, Tsang B K. p53 is required for cisplatin-induced processing of the mitochondrial fusion protein L-Opa1 that is mediated by the mitochondrial metallopeptidase Oma1 in gynecologic cancers. J Biol Chem. 2014; 289(39):27134-45.
27. Khalimonchuk O, Jeong M Y, Watts T, Ferris E, Winge D R. Selective Oma1 protease-mediated proteolysis of Cox1 subunit of cytochrome oxidase in assembly mutants. J Biol Chem. 2012; 287(10):7289-300.
28. Bohovych I, Donaldson G, Christianson S, Zahayko N, Khalimonchuk O. Stress-triggered activation of the metalloprotease Oma1 involves its C-terminal region and is important for mitochondrial stress protection in yeast. J Biol Chem. 2014; 289(19):13259-72.

What is claimed is:

1. A reporter molecule comprising:
   a) a detection domain capable of emitting a signal attached to a linker domain, the linker domain comprising;
   a Metalloendopeptidase OMA1 cleavage site;
   b) a repressor domain that represses the signal of said detection domain,
   wherein the repressor domain is operably linked to the linker domain, and
   wherein cleavage of said linker domain at said OMA1 cleavage site increases the signal of said detection domain.

2. The reporter molecule of claim 1, wherein said detection domain is a fluorescent molecule.

3. The reporter molecule of claim 2, wherein said fluorescent molecule is selected from the group consisting of 2-Am inobenzoyl (Abz), N-Methyl-antraniloyl (N-Me-ABZ), 5-(Dimethylamino)naphthalene-1-sulfonyl (Dansyl), 5-[(2-Am inoethyl)amino]-naphthalene-1-sulfonic acid (EDANS), 7-Dimethylam inocoumarin-4-acetate (DMACA), 6-Am ino-2,3-dihydro-1,3-dioxo-2-hydrazinocarbonylam ino-1H-benz[d,e]isoquinoline-5,8-disulfonic acid (*Lucifer* Yellow), Fluorescein isothiocyanate (FITC), and (7-Methoxycoumarin-4-yl)acetyl (Mca), Tryptophan (Trp).

4. The reporter molecule of claim 1, wherein the repressor domain is a fluorescent quencher.

5. The reporter molecule of claim 4, wherein said quencher is selected from the group consisting of 2,4-Dinitrophenyl (Dnp), N-(2,4-Dinitrophenyl)ethylenediamine (EDDnp), 3-Nitro-tyrosine (3-Nitro-Tyr), 4-Nitrophenylalanine (4-Nitro-Phe), para-Nitroaniline (pNA), 4-(4-Dimethylaminophenylazo)benzoyl (DABCYL), 7-Nitrobenzo[2,1,3]oxadiazol-4-yl (NBD), 4-(4-Dimethylaminophenylazo)-benzenesulfonyl, and 4-Nitrobenzyloxycarbonyl 4-Nitro Z.

6. The reporter molecule of claim 1, wherein said detection domain and said repressor domain are fluorescent polypeptides, and wherein fluorescence energy transfer occurs between said detection polypeptide and said repressor polypeptide, wherein cleavage at said OMA1 protease cleavage sites results in an alteration in fluorescence energy transfer between said reporter polypeptide and said repressor polypeptide.

7. The reporter molecule of claim 1, wherein the linker domain comprises an RA motif.

8. The reporter molecule of claim 1, wherein the linker domain is selected from the group consisting of:
   a) a polypeptide comprising the amino acid sequence set forth in SEQ ID NO:1, 2, 3, 4, 5, 6, 7, 8, 9, 10, 11, 12, 13, 14, 15, 16, 17, 18, 19, 20, 21, 22, 23, 24, 25, or 26; or
   b) a polypeptide comprising an amino acid sequence that has at least 80% sequence identity to the sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, or 26.

9. The reporter molecule of claim 1 further comprising a targeting domain, wherein said targeting domain increases the cell-penetrating ability of the reporter molecule and/or targets the reporter molecule to a sub-cellular compartment.

10. The reporter molecule of claim 9, wherein said targeting domain targets the reporter molecule to mitochondria.

11. A host cell comprising the reporter molecule of claim 1.

12. The host cell of claim 11, wherein said cell is a human cell.

13. A method of detecting mitochondrial dysfunction in a subject, comprising:
   a) obtaining a biological sample from the subject;
   b) providing the biological sample a reporter molecule comprising,
      i) a detection domain capable of emitting a signal attached to a linker domain, the linker domain comprising;
      a Metalloendopeptidase OMA1 cleavage site;
      ii) a repressor domain that represses the signal of said detection domain,
      wherein the repressor domain is operably linked to the linker domain, and
      wherein cleavage of said linker domain at said OMA1 cleavage site increases the signal of said detection domain;
   c) measuring the signal of said detection domain, and;
   d) classifying the subject with mitochondrial dysfunction when the signal of the detection domain relative to a control sample is increased.

14. The method of claim 13, wherein said biological sample is selected from the group consisting of a tissue, a tissue homogenate, cells, a cellular lysate, a tissue or cell biopsy or any combination thereof.

15. The method of claim 13, wherein the subject is suspected of suffering from a mitochondrial disorder.

16. A method of identifying compounds useful for treating mitochondrial dysfunction, comprising:
   a) contacting a biological sample with a test compound and a reporter molecule, the reporter molecule comprising,
      ii) a detection domain capable of emitting a signal attached to a linker domain, the linker domain comprising;
      a Metalloendopeptidase OMA1 cleavage site;
      ii) a repressor domain that represses the signal of said detection domain,
      wherein the repressor domain is operably linked to the linker domain, and
      wherein cleavage of said linker domain at said OMA1 cleavage site increases the signal of said detection domain;
   b) incubating the biological sample under conditions sufficient for said test compound to interact with the biological sample;
   c) measuring the signal of said detection domain, and;
   d) identifying the test compound useful for treating mitochondrial dysfunction if said signal relative to a signal of a reporter molecule in an untreated sample is decreased.

17. The method of claim 16, wherein said biological sample is selected from the group consisting of a tissue, a tissue homogenate, cells, a cellular lysate, a tissue or cell biopsy or any combination thereof.

18. The method of claim 16, wherein the test compound is selected from the group consisting of small molecules, pharmaceutically active compounds (i.e., drugs), natural products, carbohydrates, lipid molecules, amino acid derivatives, peptides, peptide mimetics, nucleic acids, antisense oligonucleotides, and microRNAs.

19. The method of claim of claim 18, wherein the test compound is a small molecule.

* * * * *

SEQUENCE LISTING

```
<160> NUMBER OF SEQ ID NOS: 34

<210> SEQ ID NO 1
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 1

Ala Phe Arg Ala Thr Asp His Gly
1               5

<210> SEQ ID NO 2
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 2

Gly Lys Thr Leu Leu Ala Arg Ala Val Ala Gly Glu Ala Asp
1               5                   10

<210> SEQ ID NO 3
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 3

Ala Leu Arg Ala Thr Asp His Gly
1               5

<210> SEQ ID NO 4
<211> LENGTH: 14
<212> TYPE: PRT
<213> ORGANISM: Artificial Sequence
```

-continued

```
<220> FEATURE:
<223> OTHER INFORMATION: SYNTHESIZED

<400> SEQUENCE: 4

Asp Arg Trp Asn Glu Ile Arg Ala Gln Leu Leu Ala Gln Met
1               5                   10

<210> SEQ ID NO 5
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 5

Leu Arg Glu Ser Tyr Glu Arg Ala Lys His Ile Leu Lys Thr
1               5                   10

<210> SEQ ID NO 6
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 6

Gln His Thr Ile Arg Ala Lys Gln Ile
1               5

<210> SEQ ID NO 7
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 7

Trp Thr Thr Arg Ala Lys Glu Arg Ala Phe Lys Gln
1               5                   10

<210> SEQ ID NO 8
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 8

Gly Val Val Asp Arg Ala Gln Ala Gly
1               5

<210> SEQ ID NO 9
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 9

His Thr Val Arg Ala Lys Gln Ile
1               5

<210> SEQ ID NO 10
<211> LENGTH: 7
<212> TYPE: PRT
<213> ORGANISM: Artificial Sequence
<220> FEATURE:
```

```
<223> OTHER INFORMATION: SYNTHESIZED

<400> SEQUENCE: 10

Asn Ser Arg Arg Ala Leu Leu
1               5

<210> SEQ ID NO 11
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 11

Trp Thr Thr Arg Ala Lys Glu Arg Ala Phe Lys Arg Gln
1               5                   10

<210> SEQ ID NO 12
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 12

Glu Glu Ile Arg Ala Val Gly Arg
1               5

<210> SEQ ID NO 13
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 13

Ser Ser Thr Arg Arg Ala Tyr Gln Gln Ile Leu
1               5                   10

<210> SEQ ID NO 14
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 14

Asn Lys Glu Arg Ala Lys Arg Glu Met
1               5

<210> SEQ ID NO 15
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 15

Gly Ala Gly Leu Arg Ala Ala Phe Gly
1               5

<210> SEQ ID NO 16
<211> LENGTH: 8
<212> TYPE: PRT
<213> ORGANISM: Artificial Sequence
<220> FEATURE:
<223> OTHER INFORMATION: SYNTHESIZED
```

<400> SEQUENCE: 16

Ile Tyr Gln Arg Ala Phe Gly Gly
1               5

<210> SEQ ID NO 17
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 17

His Arg Ile Arg Ala Lys Asn Thr
1               5

<210> SEQ ID NO 18
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 18

Ala Met Val Thr Arg Ala Gly Leu Pro
1               5

<210> SEQ ID NO 19
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 19

Val Phe Gly Arg Ala Cys Ala Leu
1               5

<210> SEQ ID NO 20
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 20

Asp Leu Arg Arg Ala Lys Asp Ile
1               5

<210> SEQ ID NO 21
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 21

Lys Thr Gly Arg Ala Asp Ile Ala Asn
1               5

<210> SEQ ID NO 22
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 22

Glu Gln Ile Arg Ala Thr Ile Glu
1               5

<210> SEQ ID NO 23
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 23

Gly Gly Arg Ala Ile Ile Thr Lys
1               5

<210> SEQ ID NO 24
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 24

Glu Trp Phe Arg Ala Gly Ser Ala
1               5

<210> SEQ ID NO 25
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 25

Lys Gly Glu Arg Ala Asp Leu Ile
1               5

<210> SEQ ID NO 26
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 26

Ala Ala Arg Ala Ala Ala Ala Ala
1               5

<210> SEQ ID NO 27
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 27

Ala Phe Lys Ala Thr Asp His Gly
1               5

<210> SEQ ID NO 28
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 28

Gly Arg Lys Lys Arg Gln Arg Arg Pro Pro Gln Pro Lys Lys
1               5                   10                  15

Lys Arg Lys Val
            20

<210> SEQ ID NO 29
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 29

Pro Leu Ser Ser Ile Phe Ser Arg Ile Gly Asp Pro Pro Lys Lys
1               5                   10                  15

Arg Lys Val

<210> SEQ ID NO 30
<211> LENGTH: 24
<212> TYPE: PRT
<213> ORGANISM: Artificial Sequence
<220> FEATURE:
<223> OTHER INFORMATION: SYNTHESIZED

<400> SEQUENCE: 30

Gly Ala Leu Phe Leu Gly Trp Leu Gly Ala Ala Gly Ser Thr Met Gly
1               5                   10                  15

Ala Pro Lys Lys Lys Arg Lys Val
            20

<210> SEQ ID NO 31
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 31

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 32
<211> LENGTH: 21
<212> TYPE: PRT
<213> ORGANISM: Artificial Sequence
<220> FEATURE:
<223> OTHER INFORMATION: SYNTHESIZED

<400> SEQUENCE: 32

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 33
<211> LENGTH: 26
<212> TYPE: PRT
<213> ORGANISM: Artificial Sequence
<220> FEATURE:
<223> OTHER INFORMATION: SYNTHESIZED

<400> SEQUENCE: 33

```
Met Leu Arg Thr Ser Ser Leu Phe Thr Arg Arg Val Gln Pro Ser Leu
1               5                   10                  15

Phe Arg Asn Ile Leu Arg Leu Gln Ser Thr
                20              25

<210> SEQ ID NO 34
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 34

Ala Thr Asp His Gly Ser Glu Ser
1               5
```